US012789001B2

(12) United States Patent
Kumar et al.

(10) Patent No.: US 12,789,001 B2
(45) Date of Patent: Nov. 10, 2026

(54) WEARABLE MEDICAL DEVICE WITH DISPOSABLE AND REUSABLE COMPONENTS

(71) Applicant: ELEMENT SCIENCE, INC., San Francisco, CA (US)

(72) Inventors: Uday N. Kumar, San Francisco, CA (US); Timothy Bahney, Edwards, CO (US); Maarten Dinger, San Francisco, CA (US); Kevin M. Farino, Medford, MA (US); Riley Marangi, San Francisco, CA (US); Jay Dhuldhoya, San Francisco, CA (US); Pedram Afshar, San Francisco, CA (US); William Stadtlander, Burlingame, CA (US)

(73) Assignee: ELEMENT SCIENCE, INC., San Francisco, CA (US)

( * ) Notice: Subject to any disclaimer, the term of this patent is extended or adjusted under 35 U.S.C. 154(b) by 157 days.

(21) Appl. No.: 18/954,331

(22) Filed: Nov. 20, 2024

(65) Prior Publication Data

US 2025/0144434 A1 May 8, 2025

Related U.S. Application Data

(63) Continuation of application No. 17/571,355, filed on Jan. 7, 2022, now Pat. No. 12,186,573, which is a (Continued)

(51) Int. Cl.
*A61N 1/04* (2006.01)
*A61B 5/274* (2021.01)
(Continued)

(52) U.S. Cl.
CPC ............ *A61N 1/3968* (2013.01); *A61B 5/274* (2021.01); *A61B 5/28* (2021.01); *A61B 5/282* (2021.01);
(Continued)

(58) Field of Classification Search
CPC .... A61N 1/3968; A61N 1/046; A61N 1/0492; A61N 1/3904; A61B 5/274; A61B 5/282;
(Continued)

(56) References Cited

U.S. PATENT DOCUMENTS 3,706,313 A 12/1972 Milani et al.
3,924,641 A 12/1975 Weiss
(Continued)

FOREIGN PATENT DOCUMENTS

CN 102316795 A 1/2012
CN 103354756 A 10/2013
(Continued)

OTHER PUBLICATIONS

3M Health Care; Tegaderm high performance foam adhesive dressing (Product Description); 8 pages retrieved from the internet (https://multimedia.3m.com/mws/media/794698O/tegaderm-hp-foam.pdf); on Sep. 22, 2021.
(Continued)

*Primary Examiner* — Eugene T Wu
(74) *Attorney, Agent, or Firm* — Shay Glenn LLP

(57) ABSTRACT

Embodiments of a wearable device are provided. The wearable device comprises a reusable component and a disposable component. The disposable component comprises a patient engagement substrate comprising adhesive on a bottom side, an electrode on the bottom side, a disposable component electrical connector, and a disposable component mechanical connector. The reusable component comprises a plurality of sealed housings mechanically coupled to
(Continued)

each other and movable with respect to each other, each of the plurality of housings containing one or more of a capacitor and a controller, a reusable component mechanical connector adapted to removably connect to the disposable component mechanical connector, and a reusable component electrical connector adapted to removably connect to the disposable component electrical connector. The device can comprise a cardiopulmonary physiologic monitor or an automatic external defibrillator, among other types of devices.

21 Claims, 28 Drawing Sheets

Related U.S. Application Data continuation of application No. 16/598,866, filed on Oct. 10, 2019, now Pat. No. 11,253,715.

(60) Provisional application No. 62/743,963, filed on Oct. 10, 2018.

(51) Int. Cl.
*A61B 5/28* (2021.01)
*A61B 5/282* (2021.01)
*A61B 5/332* (2021.01)
*A61N 1/39* (2006.01)

(52) U.S. Cl.
CPC .............. *A61B 5/332* (2021.01); *A61N 1/046* (2013.01); *A61N 1/0492* (2013.01); *A61N 1/3904* (2017.08); *A61B 2560/0443* (2013.01); *A61B 2560/0456* (2013.01); *A61B 2562/164* (2013.01); *A61B 2562/187* (2013.01); *A61B 2562/227* (2013.01)

(58) Field of Classification Search
CPC ........... A61B 5/332; A61B 2560/0443; A61B 2560/0456; A61B 2562/164; A61B 2562/187; A61B 2562/227; A61B 5/364
See application file for complete search history.

(56) References Cited

U.S. PATENT DOCUMENTS 4,023,573 A 5/1977 Pantridge et al.
4,184,493 A 1/1980 Langer et al.
4,328,808 A 5/1982 Charbonnier et al.
4,473,078 A 9/1984 Angel
4,499,907 A 2/1985 Kallok et al.
4,504,773 A 3/1985 Suzuki et al.
4,523,595 A 6/1985 Zibell
4,548,203 A 10/1985 Tacker et al.
4,574,810 A 3/1986 Lerman
4,576,170 A 3/1986 Bradley et al.
4,595,009 A 6/1986 Leinders
4,614,192 A 9/1986 Imran et al.
4,637,397 A 1/1987 Jones et al.
4,706,680 A 11/1987 Keusch et al.
4,708,145 A 11/1987 Tacker et al.
4,727,877 A 3/1988 Kallok
4,768,512 A 9/1988 Imran
4,777,954 A 10/1988 Keusch et al.
4,800,883 A 1/1989 Winstrom
4,821,723 A 4/1989 Baker et al.
4,823,796 A 4/1989 Benson
4,834,100 A 5/1989 Charms
4,850,357 A 7/1989 Bach
4,869,252 A 9/1989 Gilli
4,928,690 A 5/1990 Heilman et al.
4,953,551 A 9/1990 Mehra et al.
4,989,607 A 2/1991 Keusch et al.
4,996,984 A 3/1991 Sweeney
5,014,701 A 5/1991 Pless et al.
5,078,134 A 1/1992 Heilman et al.
5,083,562 A 1/1992 de Coriolis et al.
5,092,332 A 3/1992 Lee et al.
5,107,834 A 4/1992 Ideker et al.
5,111,813 A 5/1992 Charbonnier et al.
5,143,071 A 9/1992 Keusch et al.
5,163,427 A 11/1992 Keimel
5,172,690 A 12/1992 Nappholz et al.
5,174,288 A 12/1992 Bardy et al.
5,179,946 A 1/1993 Weiss
5,184,616 A 2/1993 Weiss
5,205,284 A 4/1993 Freeman
5,207,219 A 5/1993 Adams et al.
5,222,492 A 6/1993 Morgan et al.
5,230,336 A 7/1993 Fain et al.
5,251,624 A 10/1993 Bocek et al.
5,261,400 A 11/1993 Bardy
5,271,417 A 12/1993 Swanson et al.
5,292,338 A 3/1994 Bardy
5,314,430 A 5/1994 Bardy
5,324,309 A 6/1994 Kallok
5,334,219 A 8/1994 Kroll
5,344,429 A 9/1994 Smits
5,352,239 A 10/1994 Pless
5,360,435 A 11/1994 DeGroot
5,366,484 A 11/1994 Kroll
5,366,485 A 11/1994 Kroll et al.
5,366,497 A 11/1994 Ilvento et al.
5,372,606 A 12/1994 Lang et al.
5,381,803 A 1/1995 Herleikson et al.
5,391,186 A 2/1995 Kroll et al.
5,395,395 A 3/1995 Hedberg
5,405,366 A 4/1995 Fox et al.
5,411,547 A 5/1995 Causey
5,413,591 A 5/1995 Knoll
5,431,687 A 7/1995 Kroll
5,431,693 A 7/1995 Schroeppel
5,439,484 A 8/1995 Mehra
5,456,690 A 10/1995 Van
5,466,244 A 11/1995 Morgan
5,468,254 A 11/1995 Hahn et al.
5,474,574 A 12/1995 Payne et al.
5,483,165 A 1/1996 Cameron et al.
5,489,293 A 2/1996 Pless et al.
5,507,778 A 4/1996 Freeman
5,540,723 A 7/1996 Ideker et al.
5,540,724 A 7/1996 Cox
5,545,182 A 8/1996 Stotts et al.
5,545,183 A 8/1996 Altman
5,578,062 A 11/1996 Alt et al.
5,591,211 A 1/1997 Meltzer
5,591,212 A 1/1997 Keimel
5,594,287 A 1/1997 Cameron
5,607,454 A 3/1997 Cameron et al.
5,620,467 A 4/1997 Wagner
5,622,168 A 4/1997 Keusch et al.
5,632,267 A 5/1997 Hognelid et al.
5,643,324 A 7/1997 Persson
5,645,586 A 7/1997 Meltzer
5,650,750 A 7/1997 Leyde et al.
5,658,319 A 8/1997 Kroll
5,662,690 A 9/1997 Cole et al.
5,670,557 A 9/1997 Dietz et al.
5,674,250 A 10/1997 de Coriolis et al.
5,674,275 A 10/1997 Tang et al.
5,683,424 A 11/1997 Brown et al.
5,718,718 A 2/1998 Kroll et al.
5,720,767 A 2/1998 Amely Velez
5,725,560 A 3/1998 Brink
5,735,879 A 4/1998 Gliner et al.
5,741,306 A 4/1998 Glegyak et al.
5,766,226 A 6/1998 Pedersen
5,769,872 A 6/1998 Lopin et al.
5,792,188 A 8/1998 Starkweather et al.
5,803,927 A 9/1998 Cameron et al.
5,817,151 A 10/1998 Olson et al.

(56) References Cited

U.S. PATENT DOCUMENTS

| | | | |
|---|---|---|---|
| 5,824,017 | A | 10/1998 | Sullivan et al. |
| 5,824,018 | A | 10/1998 | Dreher et al. |
| 5,833,712 | A | 11/1998 | Kroll et al. |
| 5,849,025 | A | 12/1998 | Owens et al. |
| 5,889,388 | A | 3/1999 | Cameron et al. |
| 5,891,173 | A | 4/1999 | Brewer |
| D409,752 | S | 5/1999 | Bishay et al. |
| 5,902,249 | A | 5/1999 | Lyster |
| 5,902,323 | A | 5/1999 | Brewer et al. |
| 5,908,443 | A | 6/1999 | Brewer et al. |
| 5,928,270 | A | 7/1999 | Ramsey |
| 5,929,601 | A | 7/1999 | Kaib et al. |
| 5,944,669 | A | 8/1999 | Kaib |
| 5,951,598 | A | 9/1999 | Bishay et al. |
| 5,974,339 | A | 10/1999 | Baker et al. |
| 5,978,705 | A | 11/1999 | KenKnight et al. |
| 5,987,354 | A | 11/1999 | Cooper et al. |
| 5,991,658 | A | 11/1999 | Brewer et al. |
| 6,041,255 | A | 3/2000 | Kroll |
| 6,065,154 | A | 5/2000 | Hulings et al. |
| 6,093,982 | A | 7/2000 | Kroll |
| 6,097,982 | A | 8/2000 | Glegyak et al. |
| 6,101,413 | A | 8/2000 | Olson et al. |
| 6,104,953 | A | 8/2000 | Leyde |
| 6,108,578 | A | 8/2000 | Bardy et al. |
| 6,119,039 | A | 9/2000 | Leyde |
| 6,125,298 | A | 9/2000 | Olson et al. |
| 6,128,531 | A | 10/2000 | Campbell Smith |
| 6,134,479 | A | 10/2000 | Brewer et al. |
| 6,148,222 | A | 11/2000 | Ramsey |
| 6,148,233 | A | 11/2000 | Owen et al. |
| 6,169,387 | B1 | 1/2001 | Kaib |
| 6,173,204 | B1 | 1/2001 | Sullivan et al. |
| 6,208,896 | B1 | 3/2001 | Mulhauser |
| 6,208,898 | B1 | 3/2001 | Gliner et al. |
| 6,219,222 | B1 | 4/2001 | Shah et al. |
| 6,230,054 | B1 | 5/2001 | Powers |
| 6,234,990 | B1 | 5/2001 | Rowe et al. |
| 6,241,751 | B1 | 6/2001 | Morgan et al. |
| 6,253,099 | B1 | 6/2001 | Oskin et al. |
| 6,280,461 | B1 | 8/2001 | Glegyak et al. |
| 6,289,243 | B1 | 9/2001 | Lin et al. |
| 6,298,267 | B1 | 10/2001 | Rosborough et al. |
| 6,304,773 | B1 | 10/2001 | Taylor et al. |
| 6,304,783 | B1 | 10/2001 | Lyster et al. |
| 6,327,499 | B1 | 12/2001 | Alt |
| 6,337,995 | B1 | 1/2002 | Mower |
| 6,347,248 | B1 | 2/2002 | Gliner |
| 6,411,844 | B1 | 6/2002 | Kroll et al. |
| 6,421,563 | B1 | 7/2002 | Sullivan et al. |
| 6,441,582 | B1 | 8/2002 | Powers |
| 6,451,947 | B1 | 9/2002 | Benz et al. |
| 6,480,734 | B1 | 11/2002 | Zhang et al. |
| 6,490,478 | B1 | 12/2002 | Zhang et al. |
| 6,496,729 | B2 | 12/2002 | Thompson |
| 6,539,255 | B1 | 3/2003 | Brewer et al. |
| 6,539,258 | B1 | 3/2003 | Sullivan et al. |
| 6,546,285 | B1 | 4/2003 | Owen et al. |
| 6,546,287 | B1 | 4/2003 | Havel et al. |
| 6,549,807 | B1 | 4/2003 | Kroll |
| 6,556,863 | B1 | 4/2003 | O'Phelan et al. |
| 6,597,949 | B1 | 7/2003 | Dhurjaty |
| 6,625,487 | B2 | 9/2003 | Herleikson |
| 6,633,778 | B2 | 10/2003 | Sherman |
| 6,647,290 | B2 | 11/2003 | Wuthrich |
| 6,678,559 | B1 | 1/2004 | Breyen et al. |
| 6,681,003 | B2 | 1/2004 | Linder et al. |
| 6,687,117 | B2 | 2/2004 | Liu et al. |
| 6,738,664 | B1 | 5/2004 | McDaniel |
| 6,760,621 | B2 | 7/2004 | Walcott et al. |
| 6,766,193 | B1 | 7/2004 | Mouchawar et al. |
| 6,834,050 | B1 | 12/2004 | Madour et al. |
| 6,856,835 | B2 | 2/2005 | Bardy et al. |
| 6,871,094 | B1 | 3/2005 | Allen et al. |
| 6,873,133 | B1 | 3/2005 | Kavounas |
| 6,873,874 | B2 | 3/2005 | Ware et al. |
| 6,954,669 | B1 | 10/2005 | Fishler et al. |
| 6,963,773 | B2 | 11/2005 | Waltman et al. |
| 6,965,796 | B2 | 11/2005 | Kelly |
| 6,965,799 | B2 | 11/2005 | Nova et al. |
| 6,968,230 | B2 | 11/2005 | Waltman |
| 6,980,856 | B2 | 12/2005 | Sullivan et al. |
| 6,983,183 | B2 | 1/2006 | Thiagarajan et al. |
| 6,990,373 | B2 | 1/2006 | Jayne et al. |
| 6,993,386 | B2 | 1/2006 | Lin et al. |
| 6,996,436 | B2 | 2/2006 | Allen et al. |
| 7,006,865 | B1 | 2/2006 | Cohen et al. |
| 7,027,864 | B2 | 4/2006 | Snyder et al. |
| 7,047,072 | B2 | 5/2006 | Walker et al. |
| 7,050,850 | B2 | 5/2006 | Norton |
| 7,054,686 | B2 | 5/2006 | MacDonald |
| 7,062,321 | B2 | 6/2006 | Lyster et al. |
| 7,079,894 | B2 | 7/2006 | Lyster et al. |
| 7,085,601 | B1 | 8/2006 | Bardy et al. |
| 7,095,210 | B2 | 8/2006 | Tamura et al. |
| 7,096,062 | B2 | 8/2006 | Kelly et al. |
| 7,107,099 | B1 | 9/2006 | O'Phelan et al. |
| 7,149,576 | B1 | 12/2006 | Baura et al. |
| 7,151,963 | B2 | 12/2006 | Havel et al. |
| 7,174,204 | B2 | 2/2007 | Hadley et al. |
| 7,174,208 | B2 | 2/2007 | DeGroot et al. |
| 7,194,303 | B2 | 3/2007 | Rissmann et al. |
| 7,200,434 | B2 | 4/2007 | Havel et al. |
| 7,242,979 | B1 | 7/2007 | Kelly et al. |
| 7,245,974 | B2 | 7/2007 | Dupelle et al. |
| 7,257,441 | B2 | 8/2007 | Swerdlow et al. |
| 7,272,441 | B1 | 9/2007 | Chapman et al. |
| 7,277,751 | B2 | 10/2007 | Dupelle et al. |
| 7,379,772 | B2 | 5/2008 | Bardy et al. |
| 7,383,085 | B2 | 6/2008 | Olson |
| 7,385,802 | B1 | 6/2008 | Ribble et al. |
| 7,392,081 | B2 | 6/2008 | Wagner et al. |
| 7,463,923 | B2 | 12/2008 | Brewer et al. |
| 7,570,994 | B2 | 8/2009 | Tamura et al. |
| 7,570,996 | B2 | 8/2009 | Crespi et al. |
| 7,667,954 | B2 | 2/2010 | Lessner et al. |
| 7,684,864 | B2 | 3/2010 | Olson et al. |
| 7,706,864 | B2 | 4/2010 | Kroll et al. |
| 7,729,770 | B2 | 6/2010 | Cabelka et al. |
| 7,734,345 | B2 | 6/2010 | Cinbis |
| 7,840,265 | B2 | 11/2010 | Perschbacher et al. |
| 7,920,918 | B2 | 4/2011 | Ideker et al. |
| 7,962,207 | B2 | 6/2011 | Nassif |
| 7,974,689 | B2 | 7/2011 | Volpe et al. |
| 8,000,786 | B2 | 8/2011 | Sweeney |
| 8,024,037 | B2 | 9/2011 | Kumar |
| 8,050,759 | B2 | 11/2011 | Stegemann et al. |
| 8,086,312 | B2 | 12/2011 | Nielsen et al. |
| 8,108,043 | B2 | 1/2012 | Markowitz et al. |
| 8,116,865 | B2 | 2/2012 | Linder et al. |
| 8,121,683 | B2 | 2/2012 | Bucher et al. |
| 8,145,303 | B2 | 3/2012 | Rubin et al. |
| 8,195,280 | B2 | 6/2012 | Van Dam et al. |
| 8,209,007 | B2 | 6/2012 | McIntyre et al. |
| 8,239,012 | B2 | 8/2012 | Felix et al. |
| 8,343,644 | B2 | 1/2013 | Vaisnys et al. |
| 8,364,260 | B2 | 1/2013 | Kumar |
| 8,369,945 | B2 | 2/2013 | Youker et al. |
| 8,386,035 | B2 | 2/2013 | Vaisnys et al. |
| 8,401,637 | B2 | 3/2013 | Kroll et al. |
| 8,401,638 | B2 | 3/2013 | Swerdlow et al. |
| 8,423,136 | B2 | 4/2013 | Ostroff |
| 8,433,404 | B2 | 4/2013 | Chavan et al. |
| 8,473,051 | B1 | 6/2013 | Wessels et al. |
| 8,706,215 | B2 | 4/2014 | Kaib et al. |
| 8,838,236 | B2 | 9/2014 | Debardi et al. |
| 9,101,780 | B2 | 8/2015 | Cheng et al. |
| 9,237,858 | B2 | 1/2016 | Krusor et al. |
| 9,592,403 | B2 | 3/2017 | Sullivan |
| 9,597,004 | B2 | 3/2017 | Hughes et al. |
| 9,724,008 | B2 | 8/2017 | Sullivan et al. |
| 9,757,579 | B2 | 9/2017 | Foshee et al. |
| 9,757,580 | B2 | 9/2017 | Park et al. |
| 9,757,581 | B2 | 9/2017 | Sullivan et al. |

(56) References Cited

U.S. PATENT DOCUMENTS

| | | | |
|---|---|---|---|
| 9,789,327 | B2 | 10/2017 | Brown et al. |
| 9,827,434 | B2 | 11/2017 | Kaib et al. |
| 9,833,607 | B2 | 12/2017 | Crone et al. |
| 9,968,789 | B2 | 5/2018 | Karl et al. |
| 10,052,043 | B2 | 8/2018 | Kaib et al. |
| 10,105,547 | B2 | 10/2018 | Gustavson et al. |
| 10,252,070 | B2 | 4/2019 | Kaib et al. |
| 10,271,754 | B2 | 4/2019 | Bahney et al. |
| 10,322,291 | B2 | 6/2019 | Medema et al. |
| 10,328,275 | B2 | 6/2019 | Donnelly et al. |
| 10,953,234 | B2 | 3/2021 | Kumar et al. |
| 11,076,792 | B2 | 8/2021 | Tompkins et al. |
| 11,185,709 | B2 | 11/2021 | Kumar et al. |
| 11,253,715 | B2 | 2/2022 | Kumar et al. |
| 11,701,521 | B2 | 7/2023 | Kumar et al. |
| 11,975,209 | B2 | 5/2024 | Kumar et al. |
| 12,186,573 | B2 | 1/2025 | Kumar et al. |
| 2001/0037093 | A1 | 11/2001 | Benkowski et al. |
| 2002/0188216 | A1 | 12/2002 | Kayyali et al. |
| 2003/0055460 | A1 | 3/2003 | Owen et al. |
| 2003/0095648 | A1 | 5/2003 | Kaib et al. |
| 2003/0125771 | A1 | 7/2003 | Garrett |
| 2003/0167075 | A1 | 9/2003 | Fincke |
| 2003/0201752 | A1 | 10/2003 | Locke et al. |
| 2004/0143297 | A1 | 7/2004 | Ramsey |
| 2004/0267322 | A1 | 12/2004 | Kavounas et al. |
| 2005/0070963 | A1 | 3/2005 | Wilson et al. |
| 2005/0090868 | A1 | 4/2005 | Cansell |
| 2005/0107833 | A1 | 5/2005 | Freeman et al. |
| 2005/0131465 | A1 | 6/2005 | Freeman et al. |
| 2005/0234515 | A1 | 10/2005 | Freeman |
| 2006/0116724 | A1 | 6/2006 | Snyder |
| 2006/0129192 | A1 | 6/2006 | Greatbatch et al. |
| 2006/0149346 | A1 | 7/2006 | Dupelle et al. |
| 2006/0173499 | A1 | 8/2006 | Hampton et al. |
| 2006/0178706 | A1 | 8/2006 | Lisogurski et al. |
| 2006/0229679 | A1 | 10/2006 | Joo |
| 2006/0241700 | A1 | 10/2006 | Ghanem et al. |
| 2006/0259091 | A1 | 11/2006 | Ries et al. |
| 2006/0285302 | A1 | 12/2006 | Kim |
| 2007/0100381 | A1 | 5/2007 | Snyder et al. |
| 2008/0177342 | A1 | 7/2008 | Snyder |
| 2008/0183230 | A1 | 7/2008 | Kemmetmueller et al. |
| 2008/0255625 | A1 | 10/2008 | Powers |
| 2008/0312708 | A1 | 12/2008 | Snyder |
| 2009/0005827 | A1 | 1/2009 | Weintraub et al. |
| 2009/0076345 | A1 | 3/2009 | Manicka et al. |
| 2009/0076559 | A1 | 3/2009 | Libbus et al. |
| 2009/0306730 | A1 | 12/2009 | Roso |
| 2010/0030290 | A1 | 2/2010 | Bonner et al. |
| 2010/0241181 | A1 | 9/2010 | Savage et al. |
| 2010/0292544 | A1 | 11/2010 | Sherman et al. |
| 2011/0071611 | A1 | 3/2011 | Khuon et al. |
| 2011/0125040 | A1 | 5/2011 | Crawford et al. |
| 2011/0279963 | A1 | 11/2011 | Kumar et al. |
| 2011/0288604 | A1 | 11/2011 | Kaib et al. |
| 2012/0025521 | A1 | 2/2012 | Baller et al. |
| 2012/0046706 | A1 | 2/2012 | Anderson et al. |
| 2012/0089037 | A1 | 4/2012 | Bishay et al. |
| 2012/0116472 | A1 | 5/2012 | Pittaro |
| 2012/0158075 | A1 | 6/2012 | Kaib et al. |
| 2012/0169287 | A1 | 7/2012 | Lopin et al. |
| 2012/0191149 | A1 | 7/2012 | Freeman |
| 2012/0197353 | A1 | 8/2012 | Donnelly et al. |
| 2012/0215123 | A1 | 8/2012 | Kumar et al. |
| 2012/0265264 | A1 | 10/2012 | Vaisnys et al. |
| 2012/0289809 | A1 | 11/2012 | Kaib et al. |
| 2012/0302860 | A1 | 11/2012 | Volpe et al. |
| 2012/0325096 | A1 | 12/2012 | Holt |
| 2013/0018432 | A1 | 1/2013 | Garrett et al. |
| 2013/0053909 | A1 | 2/2013 | Elghazzawi et al. |
| 2013/0085538 | A1 | 4/2013 | Volpe et al. |
| 2013/0123870 | A1 | 5/2013 | Heinrich et al. |
| 2013/0158614 | A1 | 6/2013 | Azar et al. |
| 2013/0325096 | A1 | 12/2013 | Dupelle et al. |
| 2014/0025131 | A1 | 1/2014 | Sullivan et al. |
| 2014/0039594 | A1 | 2/2014 | Savage et al. |
| 2014/0207201 | A1 | 7/2014 | Piha et al. |
| 2014/0243694 | A1 | 8/2014 | Baker et al. |
| 2014/0277226 | A1 | 9/2014 | Poore et al. |
| 2014/0371806 | A1 | 12/2014 | Raymond et al. |
| 2014/0378782 | A1 | 12/2014 | Herken et al. |
| 2015/0148854 | A1 | 5/2015 | Whiting et al. |
| 2015/0217121 | A1 | 8/2015 | Subramanian et al. |
| 2015/0238094 | A1 | 8/2015 | Lai et al. |
| 2015/0321022 | A1 | 11/2015 | Sullivan et al. |
| 2015/0335288 | A1 | 11/2015 | Toth et al. |
| 2017/0056682 | A1 | 3/2017 | Kumar et al. |
| 2018/0093090 | A1 | 4/2018 | Desmarais |
| 2022/0088371 | A1 | 3/2022 | Freeman |
| 2024/0091545 | A1 | 3/2024 | Kumar et al. |
| 2024/0359024 | A1 | 10/2024 | Kumar et al. |
| 2025/0360328 | A1 | 11/2025 | Kumar et al. |
| 2026/0061208 | A1 | 3/2026 | Kumar et al. |

FOREIGN PATENT DOCUMENTS

| | | | | |
|---|---|---|---|---|
| CN | 103405851 | A | 11/2013 | |
| CN | 103443794 | A | 12/2013 | |
| CN | 106470593 | A | 3/2014 | |
| EP | 95726 | B1 | 11/1988 | |
| EP | 362093 | A2 | 4/1990 | |
| EP | 445800 | A1 | 9/1991 | |
| EP | 487776 | A1 | 6/1992 | |
| EP | 612253 | A1 | 8/1994 | |
| EP | 503778 | B1 | 7/1996 | |
| EP | 469817 | B1 | 2/1997 | |
| EP | 465241 | B1 | 11/1998 | |
| EP | 589251 | B1 | 11/2000 | |
| EP | 1263497 | A1 | 12/2002 | |
| EP | 988087 | B1 | 1/2003 | |
| EP | 998328 | B1 | 10/2003 | |
| EP | 687479 | B1 | 8/2004 | |
| EP | 973582 | B1 | 5/2005 | |
| EP | 888149 | B1 | 7/2005 | |
| EP | 1742700 | A2 | 1/2007 | |
| EP | 1759732 | A1 | 3/2007 | |
| EP | 1827594 | A1 | 9/2007 | |
| EP | 1954345 | A2 | 8/2008 | |
| EP | 2047886 | A1 | 4/2009 | |
| EP | 1530983 | B1 | 9/2009 | |
| EP | 2446927 | A1 | 5/2012 | |
| JP | H04184831 | A | 7/1992 | |
| JP | H06105917 | A | 4/1994 | |
| JP | H07541 | A | 1/1995 | |
| JP | H10509334 | A | 9/1998 | |
| JP | 2002514107 | | 5/2002 | |
| JP | 2007150180 | A | 6/2007 | |
| JP | 2008520306 | A | 6/2008 | |
| JP | 2013542787 | | 11/2013 | |
| JP | 2014533525 | A | 12/2014 | |
| JP | 2015521085 | A | 7/2015 | |
| JP | 2017506121 | | 3/2017 | |
| JP | 2018508325 | A | 3/2018 | |
| WO | WO97/031680 | A1 | 9/1997 | |
| WO | WO2001/085251 | A1 | 11/2001 | |
| WO | WO2006/115778 | A2 | 11/2006 | |
| WO | WO2007/092543 | A2 | 8/2007 | |
| WO | WO2007/113452 | A1 | 10/2007 | |
| WO | WO2010/096774 | A2 | 8/2010 | |
| WO | WO2011/163339 | A1 | 12/2011 | |
| WO | WO2013/033238 | A1 | 3/2013 | |
| WO | WO2013/181607 | A1 | 12/2013 | |
| WO | WO2014/007307 | A1 | 1/2014 | |
| WO | WO2014/151925 | A1 | 9/2014 | |
| WO | WO2014/160848 | A1 | 10/2014 | |
| WO | WO2015/017727 | A1 | 2/2015 | |
| WO | WO-2017035502 | A1 * | 3/2017 | ........... A61B 5/0205 |

OTHER PUBLICATIONS

Aliexpress; Car wrapping cut tool double head carbon vinyl film cutter knife with paperback slitter blade mo-110S; 4 pages; retrived

(56) References Cited

OTHER PUBLICATIONS from the internet (https://www.aliexpress.us/item/2261800118493818.html?gatewayAdapt=glo2usa4itemAdapt) on Apr. 2021.

Birgersdotter-Green; Advances in AEDs and wearable defibrillators (presentation slides): 23 pages; 2013 (year of pub. sufficiently earlier than effective US filing date and any foreign priority date; available to applicants(s) at least as of Jun. 4, 2013).

Calle et al.; Equivalence of the standard monophasic waveform shocks delivered by automated external defibrillators; Resuscitation; 53(1); pp. 41-46; Apr. 2002.

Caterham; Half-side screen with armrests, left carbon vinyl, S3, R500; 6 pages; retrieved from the internet (https://caterhamshop.official.ec/items/23847744) on Apr. 21, 2023.

Field et al.; Part 1: Executive Summary: 2010 American heart association guidelines for cardiopulmonary resuscitation and emergency cardiovascular care; Circulation; 122 (18 Suppl. 3); pp. S640-S656; Nov. 2, 2010.

International Chemical Co.; Saturated silver/silver chloride reference electrode with double junction holder; 1 page; retrieved from the internet (https://www.autolabj.com/construction.files/electrode.files/E-agagcl.htm) on Apr. 21, 2023.

Jones et al.; improved safety factor for triphasic defibrillator waveforms; Cir. Res.; 64(6); pp. 1172-1177; Jun. 1989.

Jones et al.; Increasing fibrillation duration enhances relative asymmetrical biphasic versus monophasic defibrillator waveform efficacy; Circ. Res.; 67(2); pp. 376-384; Aug. 1990.

Kotobank; Silver-silver chloride electrode; 3 pages; retrieved from the internet (https://kotobank.jp/word/%E9%8A%80-%E5%A1%A9%E5%80%96%E9%8A%80%E9%9B%BB%E6%A5%B5-764277) on May 1, 2023.

Pariaut et al; Evaluation of shock waveform configuration on the defibrillation capacity of implantable cardioverter defibrillators in dogs; J. Vet. Cardiol.; 14(3); pp. 389-398; Sep. 2012.

Swartz et al.; Conditioning prepulse of biphasic defibrillator waveforms enhances refractoriness to fibrillation wavefronts; Circulation Res.; 68(2); pp. 438-449; Feb. 1991.

Walsh et al.; Novel rectangular biphasic and monophasic waveforms delivered by a radiofrequency-powered defibrillator compared with conventional capacitor-based waveforms in transvenous cardioversion of atrial fibrillation; Europace; 8(10); pp. 873-880; Oct. 2006.

Zipes et al.; ACC/AHA/ESC 2006 guidelines for management of patients with ventricular arrhythmias and the prevention of sudden cardiac death; Europace; 8(9); pp. 746-837; Sep. 2006.

Zoll; LifeVest model 4000 Patient Manual; 16 pages retrieved from the internet (https://www.accessdata.fda.gov/cdrh_docs/pdf/P010030S056c.pdf0; on Sep. 22, 2021.

* cited by examiner

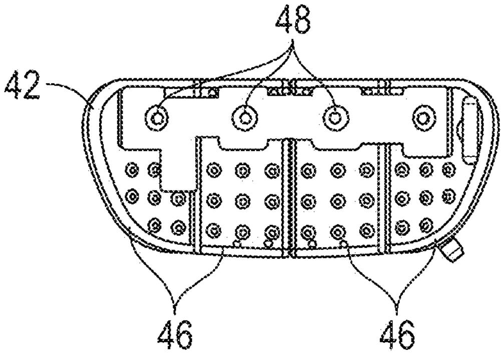
FIG. 4A
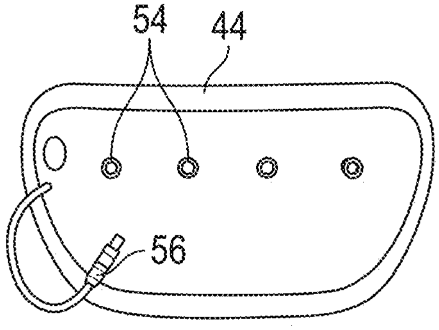
FIG. 4B
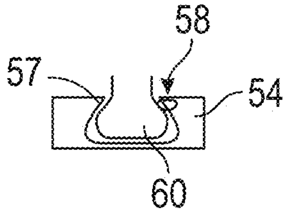
FIG. 4C
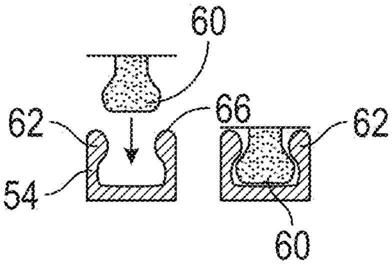
FIG. 4F
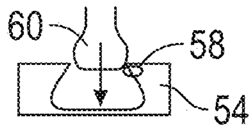
FIG. 4D
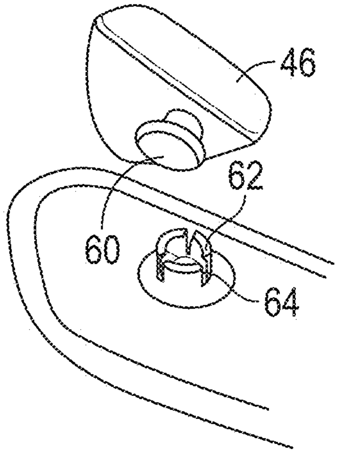
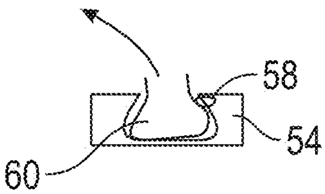
FIG. 4E
FIG. 4G

+

=

FIG. 10A
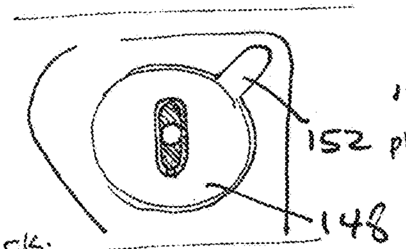
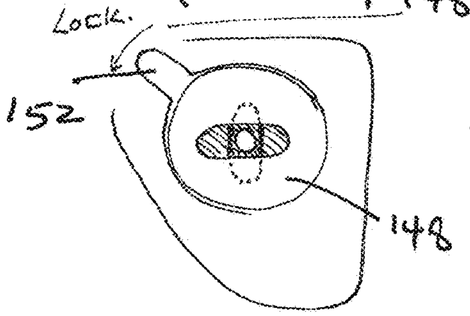
FIG. 10B
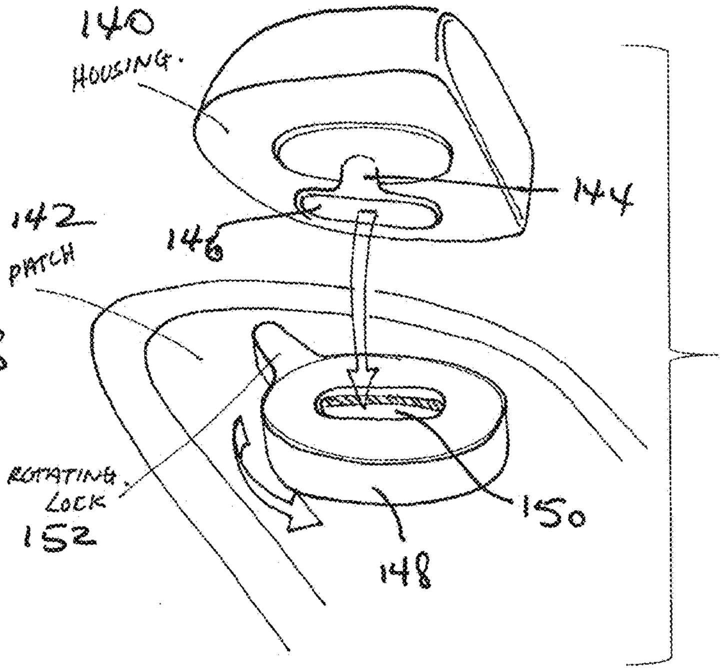
FIG. 10C

WEARABLE MEDICAL DEVICE WITH DISPOSABLE AND REUSABLE COMPONENTS

CROSS REFERENCE TO RELATED APPLICATIONS

This application is a continuation of U.S. application Ser. No. 17/571,355, filed Jan. 7, 2022, which is a continuation of U.S. application Ser. No. 16/598,866, filed Oct. 10, 2019, now U.S. Pat. No. 11,253,715, which claims the benefit of U.S. Provisional Patent Application No. 62/743,963, filed Oct. 10, 2018, the entire disclosures of which are incorporated by reference herein.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present disclosure relates generally to wearable devices, such as external cardiopulmonary physiologic monitors or defibrillators. In particular, the disclosure relates to automatic external cardiopulmonary physiologic monitors or defibrillators that can be continuously and comfortably worn by a patient for an extended period of time.

BACKGROUND

International Patent Publication No. WO2017/035502 discloses multiple embodiments of an external defibrillator that is adhesively attached to the patient and that can be comfortably worn around the clock during showering, sleeping and normal activities. The adhesive patches and batteries of these devices may have useful lives that are shorter than the other components of the defibrillator. In addition, the patient may need to wear the defibrillator beyond the ends of the useful lives of the adhesive patches and/or batteries.

SUMMARY OF THE DISCLOSURE

The present invention relates generally to wearable devices (such as wearable external cardiopulmonary physiologic monitors or defibrillators) whose batteries and/or adhesive patient engagement substrate(s) can be safely and easily changed by the patient. One aspect of the invention provides a wearable device having a reusable component and a disposable component, the disposable component having a patient engagement substrate with adhesive on a bottom side, an electrode on the bottom side, a disposable component electrical connector, and a disposable component mechanical connector, the reusable component having a plurality of sealed housings mechanically coupled to each other and movable with respect to each other, each of the plurality of housings containing one or more of a capacitor and a controller, a reusable component mechanical connector adapted to removably connect to the disposable component mechanical connector, and a reusable component electrical connector adapted to removably connect to the disposable component electrical connector.

In some embodiments, the reusable component further includes a flexible circuit configured to provide electrical communication among electrical components within the housings. The flexible circuit may optionally be affixed to back surfaces of the plurality of housings. Additionally or alternatively, the flexible circuit may optionally be overmolded with flexible material to prevent water ingress.

In some embodiments, the disposable component also includes a battery (such as, e.g., a rechargeable battery) disposed in a battery housing, a battery electrical connector configured to electrically connect the battery to, and disconnect the battery from, the capacitor and/or controller, and a battery mechanical connector adapted to removably connect the battery housing to the reusable component. In such embodiments, the battery mechanical connector may optionally include a cradle dock. The battery housing may also be removably connectable to a top side of the patient engagement substrate via the battery mechanical connector. The reusable component may also optionally include an alarm adapted to indicate that a battery has not been connected to the reusable component.

In some embodiments, the disposable component also includes a battery disposed in a battery housing, a battery electrical connector configured to be connected to, and disconnected from, the reusable component electrical connector, a battery mechanical connector adapted to removably connect the battery housing to the reusable component, and a cable configured to be connected to, and disconnected from, the disposable component electrical connector.

In embodiments in which the battery is a rechargeable battery, the reusable component may also include a port for a battery charger. Alternatively or additionally, the wearable device may also have a wireless battery charger.

In some embodiments, the reusable component may include a housing support, the housings being mechanically connected to a top side of the housing support, the reusable component mechanical connector being disposed on a bottom side of the housing support. The disposable component of such embodiments may also include a battery disposed in a battery housing, a battery electrical connector configured to electrically connect the battery to, and disconnect the battery from, the capacitor, and a cradle dock adapted to removably connect the battery housing to the housing support.

In some embodiments, the disposable component further comprises a battery permanently attached to the disposable component.

In some embodiments, at least one of the disposable component mechanical connector and the reusable component mechanical connector includes a magnet. The magnet may be, e.g., disposed in a housing extending from the reusable component, the housing comprising an opening through which the disposable component mechanical connector can be inserted and moved to contact the magnet. Alternatively, the magnet may be disposed in a housing extending from the disposable component, the housing comprising an opening through which the reusable component mechanical connector can be inserted and moved to contact the magnet.

In some embodiments, the disposable component mechanical connector and the reusable component mechanical connector together comprise male and female mechanical snap components, male and female mechanical slide locking components, adhesive and a removable adhesive cover, a hook and loop connector, a key and a rotatable lock, a breakable component adapted to break to disconnect the disposable component mechanical connector from the reusable component mechanical connector, a removable component adapted to disconnect the disposable component mechanical connector from the reusable component mechanical connector, or a release latch adapted to disconnect the disposable component mechanical connector from the reusable component mechanical connector.

In some embodiments, the disposable component mechanical connector includes a spring-biased latch and the reusable component mechanical connector includes a cavity adapted to receive the latch. In some such embodiments, the disposable component mechanical connector may further include a latch actuator operably connected to move the latch to connect the disposable component mechanical connector to, or disconnect the disposable component mechanical connector from, the reusable component mechanical connector.

In some embodiments, the disposable component mechanical connector and the reusable component mechanical connector are configured to allow the reusable component and the disposable component to move relative to one another while still maintaining a mechanical connection.

In some embodiments, at least one of the disposable component mechanical connector and the reusable component mechanical connector also includes an alignment tool or mechanism adapted to align the disposable component mechanical connector and the reusable component mechanical connector. In some such embodiments, the alignment mechanism or tool includes a reusable component support adapted to hold the reusable component and a disposable component support adapted to hold the patient engagement substrate, the alignment tool having a first configuration in which a reusable component may be supported in the reusable component support apart from a disposable component disposed in the disposable component support and a second configuration in which reusable component mechanical connectors of a reusable component supported in the reusable component support are in contact with the disposable component mechanical connectors of a disposable component disposed in the disposable component support.

In some embodiments, the disposable component mechanical connector and the reusable component mechanical connector together comprise a buckle and a buckle connector. In some such embodiments, the disposable component mechanical connector and the reusable component mechanical connector together further comprise a buckle release mechanism. In some such embodiments, the buckle is disposed on the patient engagement substrate and the buckle connector and buckle release are disposed on the reusable component, the buckle release being accessible for actuation only if the patient engagement substrate is bent.

In some embodiments, the disposable component mechanical connector is disposed on a support element pivotably attached to the patient engagement substrate.

In some embodiments, the patient engagement substrate has a first configuration in which a connection between the disposable component mechanical connector and the reusable component mechanical connector is maintained and a second configuration in which the disposable component mechanical connector may be disconnected from the reusable component mechanical connector.

Some embodiments also include a tool adapted to disconnect the reusable component mechanical connector from the disposable component mechanical connector. Such embodiments may also have a tool access point on the reusable component mechanical connector, the patient engagement substrate having a first configuration in which the disposable component mechanical connector is connected to the reusable component mechanical connector and the patient engagement substrate blocks the tool access point and a second configuration in which the disposable component mechanical connector is connected to the reusable component mechanical connector and the patient engagement substrate does not block the tool access point.

In some embodiments, when connected, the disposable component electrical connector and the reusable component electrical connector provide a waterproof electrical connection.

In some embodiments, the disposable component electrical connector and the reusable component electrical connector together comprise a cable, a plug at a distal end of the cable and a receptacle adapted to receive the plug. In some such embodiments, the cable may extend from the disposable component and the receptacle is disposed on the reusable component. The receptacle may optionally extend from one of the plurality of housings, or the receptacle may optionally extend from a flexible circuit configured to provide electrical communication among electrical components within the housings.

In embodiments in which the disposable component electrical connector and the reusable component electrical connector together comprise a cable, a plug at a distal end of the cable and a receptacle adapted to receive the plug, the cable may extend from the reusable component, and the receptacle may be disposed on the disposable component. In some such embodiments, the cable may extend from one of the plurality of housings or from a flexible circuit configured to provide electrical communication among electrical components within the housings.

In embodiments in which the disposable component electrical connector and the reusable component electrical connector together comprise a cable, a plug at a distal end of the cable and a receptacle adapted to receive the plug, the disposable component electrical connector and the reusable component electrical connector together further comprise a second cable, the receptacle being disposed at a distal end of the second cable.

In some embodiments, the disposable component electrical connector is integrated with the disposable component mechanical connector and the reusable component electrical connector is integrated with the reusable component mechanical connector. In some such embodiments, the disposable component electrical connector and the reusable component electrical connector are adapted to slide with respect to each other to make electrical and mechanical connections. In other such embodiments, the disposable component electrical connector and the reusable component electrical connector are adapted to snap together to make electrical and mechanical connections. In some such embodiments, a mechanical connection between the disposable component mechanical connector and the reusable component electrical connector prevents disposable component electrical connector from being disconnected from the reusable component electrical connector.

In some embodiments, the disposable component also includes one or more of the following: an electronic memory adapted to receive and store user data from the controller; a mechanical connection indicator adapted to indicate a mechanical connection between the disposable component mechanical connector and the reusable component mechanical connector, and an electrical connection indicator adapted to indicate an electrical connection between the disposable component electrical connector and the reusable component electrical connector.

In some embodiments, the disposable component also includes a second patient engagement substrate having an electrode on a bottom side and a second patient engagement substrate electrical connector.

In some embodiments, the wearable device is a cardiopulmonary physiologic monitor and/or an automatic external defibrillator.

In some embodiments, the reusable component mechanical connector and the disposable component mechanical connector comprise a trigger prevention mechanism configured to prevent disconnection of the reusable component mechanical connector and the disposable component mechanical connector. In some such embodiments, the trigger prevention mechanism comprises a protruding feature on the reusable component mechanical connector configured to interact with an opening or depression on the disposable component mechanical connector. In some embodiments, the trigger prevention mechanism comprises a protruding feature on the disposable component mechanical connector configured to interact with an opening or depression on the reusable component mechanical connector. In some embodiments, the trigger prevention mechanism is configured to be disengaged by bending a portion of at least one of the disposable component mechanical connector and the reusable component mechanical connector.

In some embodiments, the wearable device comprises a mechanism that can be manually triggered in order to initiate, activate, or override a device function. In some such embodiments, the mechanism can be manually triggered to override delivery of therapy. In some embodiments, the mechanism can be manually triggered to initiate a device status check. In some embodiments, the mechanism can be manually triggered to activate the device.

Another aspect of the invention provides a method of using a wearable device having a first disposable component comprising a patient engagement substrate comprising adhesive and an electrode on a bottom side and a reusable component comprising a plurality of sealed housings mechanically and electrically coupled to the disposable component, each of the plurality of housings containing one or more of a capacitor, batteries, or a controller. In some embodiments, the method includes the steps of adhering the wearable device to a skin surface portion of a patient for a first time period; monitoring patient ECG signals with the controller and the electrode during the first time period; removing the wearable device from the skin surface portion of the patient at the end of the first time period; mechanically and electrically disconnecting the disposable component from the reusable component; mechanically and electrically connecting to the reusable component a second disposable component comprising a patient engagement substrate comprising adhesive and electrodes on a bottom side; applying the second disposable component to a skin portion of the patient; and monitoring patient ECG signals using the controller and the electrode of the second disposable component.

In embodiments in which the disposable component further comprises a battery disposed in a battery housing, the method also includes the step of electrically disconnecting the battery from the reusable component and connecting a replacement battery to the reusable connection. In some embodiments, the step of electrically disconnecting the battery from the reusable component is performed after the step of removing the wearable device from the skin surface portion of the patient. In embodiments in which the replacement battery is disposed in a replacement battery housing, the method further includes the step of mechanically connecting the replacement battery housing to the reusable component. The method may also include the step of providing an alarm if the battery or a replacement battery is not connected to the reusable component.

In embodiments in which the reusable component includes a rechargeable battery, the method further includes the step of recharging the rechargeable battery.

In some embodiments, the step of mechanically and electrically disconnecting the disposable component from the reusable component includes the step of bending the patient engagement substrate, breaking a structural element, or operating a release mechanism (such as, e.g., a release latch, a squeeze buckle, or a push button).

In some embodiments, the method also includes the step of using an alignment tool to align the second disposable component with the reusable component prior to mechanically and electrically connecting the reusable component to the second disposable component.

Some embodiments of the method include the step of preventing electrical disconnection of the disposable component from the reusable component before mechanical disconnection of the disposable component from the reusable component.

Some embodiments of the method include the step of providing an indication of mechanical connection between the disposable component and the reusable component.

In some embodiments, the wearable device is a cardiopulmonary physiologic monitor and/or an automatic external defibrillator.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-G show embodiments of mechanical connectors for connecting and disconnecting a reusable component of a wearable device to a disposable component of the wearable device.

FIGS. 10A-C show embodiments of mechanical connectors for connecting and disconnecting a reusable component of a wearable device to a disposable component of the wearable device.

DETAILED DESCRIPTION

Figure 1A:
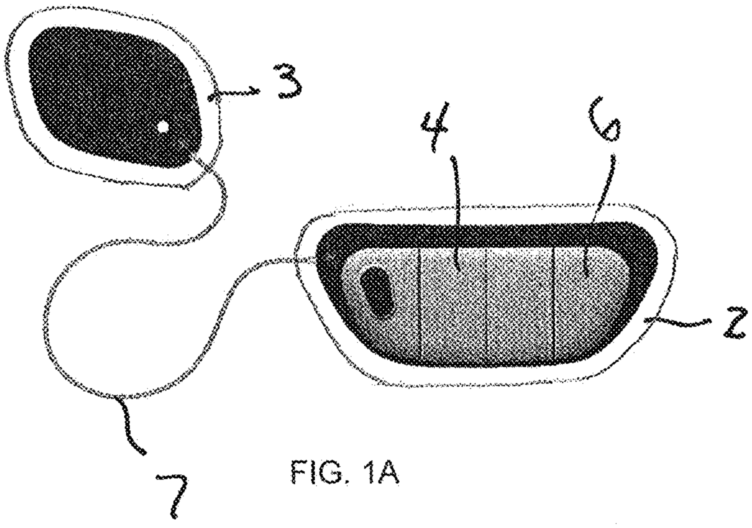
FIGS. 1A-D show a wearable device having reusable and disposable components.
Figure 1D:
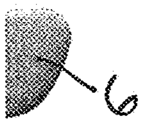
Figure 1B:
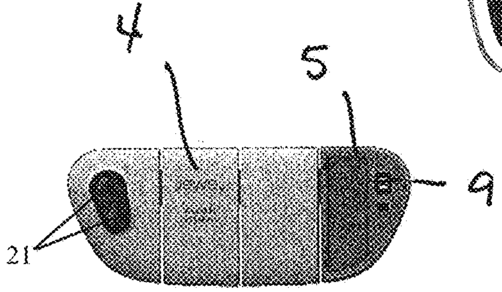

Embodiments of the invention provide an adhesively mounted wearable device, such as an external cardiopulmonary physiologic monitor or cardioverter/defibrillator similar to those shown in WO2017/035502, whose adhesive patient engagement substrate(s) and battery can be mechanically and electrically attached and detached from the device's reusable electronics. In particular, the devices of this invention enable a user, particularly a patient with low dexterity, poor hand/arm strength, poor vision, etc., to perform the following steps prior to wearing the device: (1) mechanically attach reusable electronics to adhesive patient engagement substrate(s); (2) electrically connect reusable electronics to adhesive patient engagement substrate(s); (3) mechanically attach a battery to the reusable electronics; and (4) electrically connect the battery to the reusable electronics. These embodiments provide waterproof electrical connections, enabling the patient to shower and perform other activities while wearing the device. The mechanical and electrical connections of these various embodiments can also withstand expected mechanical forces without detaching or disconnecting, such as when the patient moves or changes position (e.g., sits up, lies down, falls, walks), when the device engages another object (e.g., engaging a seatbelt or clothing covering the device). Embodiments of the invention provide mechanical and electrical connections between disposable and reusable components that are difficult or impossible to disconnect while the device is being worn by the patient.

Embodiments of the reusable component of the wearable device of this invention have multiple housings or modules each containing one or more electrical components. For example, in embodiments in which the wearable device is a cardioverter/defibrillator similar to those shown in WO2017/035502, the housings or modules may each contain one or more of a controller and a capacitor. In these embodiments, a flexible electrical circuit extends between the housings or modules to provide connections among the electronic components. The flexible electrical circuit may be waterproof or covered with waterproof material. In addition, in embodiments of the invention the flexible circuit can withstand the flexing twisting, stretching, bending, compression, tension, etc., that may come from patient movement while wearing the wearable device. In some embodiments, the flexible electrical circuit is exterior to the housings or modules, and waterproof electrical connections extend from the flexible electrical circuit to the electrical components in the housings or modules. In other embodiments, the flexible electrical circuit is at least partially inside one or more of the housings or modules.

An illustrative example of a wearable device having reusable and disposable components is shown in FIGS. 1A-D. In this example, the wearable device is an external cardiopulmonary physiologic monitor or cardioverter/defibrillator similar to those shown in WO2017/035502 having a first adhesive patient engagement substrate 2, a second adhesive patient engagement substrate 3, a plurality of housings 4 mounted on a housing base 5, a battery housing 6 containing a battery, a cable 7 extending between patient engagement substrates 2 and 3, mechanical connectors 8 for attaching the housing base 5 to the first patient engagement substrate 2, an electrical connector 1 for connecting the electrical components in housings 4 to the first patient engagement substrate and an electrical connector 9 for electrically connecting the battery housing 6 to the other housings 4. The housings 4 each contain one or more of a controller, a capacitor or other cardiopulmonary physiologic monitor or defibrillator electronics, and the housings 4 together with their base 5 form the reusable component of the wearable device 1. The first and second adhesive patient engagement substrates each have one or more electrodes on their bottom sides which, when the substrates 2 and 3 are connected to the housings 4, can sense cardiac activity or, in the case of a cardioverter/defibrillator, deliver a shock from the defibrillator components to a patient to whom the substrates are adhesively attached. The first and second patient engagement substrates and the battery in the battery housing are the disposable components of the wearable device. The wearable device can comprise override functionality for overriding a scheduled or already initiated device function or therapy. For example, in the case of a cardioverter/defibrillator, the device can be controlled to cancel a scheduled shock. In some embodiments, the same buttons can also be used to interact with various user interface prompts, as needed (e.g., turn on, perform status check, etc.). Controls or buttons 21 on the reusable component can be pressed simultaneously to initiate the override function. Other mechanisms for initiating the override are also possible (e.g., buttons located on opposing surfaces of the housings and configured to be squeezed or pinched simultaneously, buttons located on other surfaces of the wearable device such as the first or second patient engagement substrate, etc.).

Various mechanical connectors, electrical connectors and device configurations are described below. Each can be used in combination with others.

One aspect of the invention is the manner in which reusable component(s) of a wearable device may be mechanically connected to, and disconnected from, disposable component(s). Embodiments of the invention provide robust, intuitive, simple to operate (even for patients with low dexterity), load-bearing mechanical attachment between the reusable component of a wearable device (such as, e.g., an external cardiopulmonary physiologic monitor or cardioverter/defibrillator similar to those shown in WO2017/035502) and a disposable component of that device (such as, e.g., an adhesively attachable patient engagement substrate and/or a battery). In many of the embodiments, the reusable component can be detached from the disposable component only when the wearable device is not being worn by the patient. The mechanical attachment mechanisms described herein can be used in combination with each other and with any of the embodiments described in this disclosure.

Figure 2A:
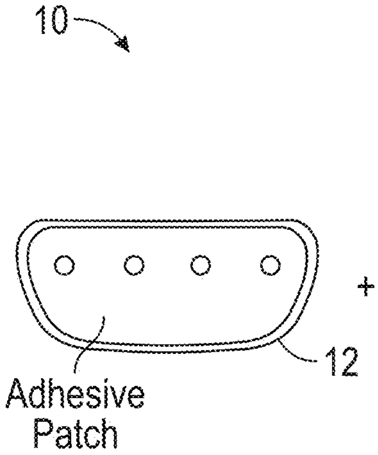
FIGS. 2A-E show an embodiment of a wearable device employing magnets as mechanical connectors.
Figure 2B:
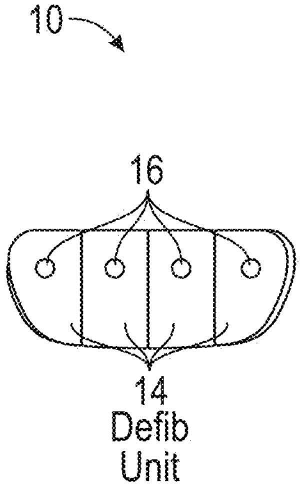
Figure 2C:
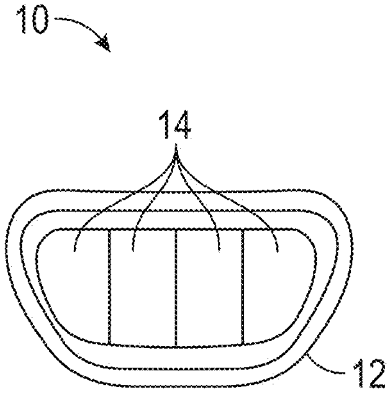
Figure 2D:
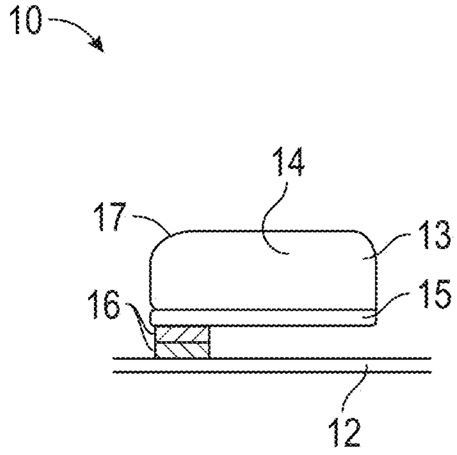

FIGS. 2A-E show an embodiment employing magnets as mechanical connectors. In the illustrated embodiment, the wearable device 10 is an external cardiopulmonary physiologic monitor or cardioverter/defibrillator similar to those shown in WO2017/035502. Components of the wearable device 10 include a first patient engagement substrate 12, a plurality of housings 14, and a second patient engagement substrate (not shown). A front view is shown in FIGS. 2A and 2C; and a back view is shown in FIG. 2B. The housings 14 can comprise a top 13 and bottom 15. The first patient engagement substrate 12 and the second patient engagement substrate each include an adhesive for attaching the substrate to the patient and one or more electrodes (not shown) for sensing cardiac activity or, in the case of a cardioverter/defibrillator, delivering an electrical shock to the patient. The housings 14 each contain one or more of a battery, a capacitor or a controller. In this embodiment, housings 14 are movable with respect to each other and are in electrical communication with each other via, e.g., a flexible circuit (not shown). The electrical components within the housings are also in electrical communication with the electrodes in the first and second patient engagement substrates after the housings have been attached to the first patient engagement substrate, e.g., in a manner described further below. The reusable component of wearable device 10 includes housings 14, and the disposable component includes the first patient engagement substrate 12 and the second patient engagement substrate. The patient engagement substrate 12 can comprise a patch, as shown in FIG. 2D.

Figure 1C:
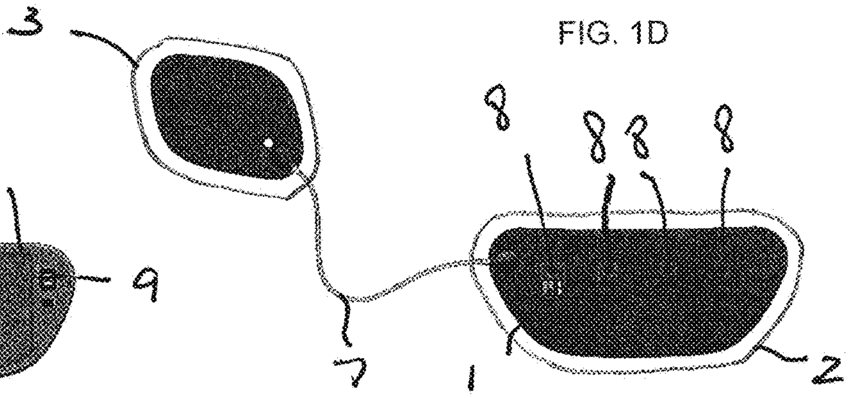

As shown in FIGS. 2A-E, magnets 16 are disposed on the top side 15 of patient engagement substrate 12 and on the bottom side 16 of housings 14 in corresponding positions that enable the housings to be mounted to the first patient engagement substrate as shown in FIG. 1C. The magnets must be strong enough to support the weight of the housings and to withstand dislodging resulting from patient movement, snagging on clothing or other objects, etc., while still enabling intended detachment of the housings from the patient engagement substrate. In this embodiment, the magnets are disposed closer to the top 17 of housings 14 so that the housings can serve as lever arms to facilitate separation of the patient engagement substrate's magnets from the housings' magnets. As an example, the magnets 16 shown in FIGS. 2D-E each have surface areas of 1 square inch and have a magnetic attachment strength of 20 lbs, which can create a radius $r_A$ around the axis of rotation A of 0.5 in. The housing 14 has a length of 2.5 inches, which can create a radius $r_R$ around the axis of rotation A of 2.5 in. The removal force $F_R$ applied to the end of the moment arm of the housing

Figure 2E:
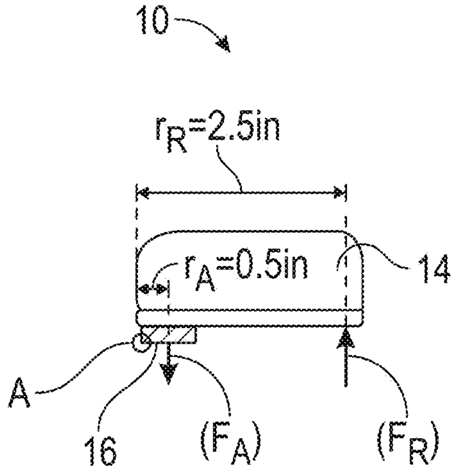

14 (as shown in FIG. 2E) to separate the magnets 16 is 4 lbs.—only 20% of the attachment force ($F_A$), which is 20 lbs.

Figure 3A:
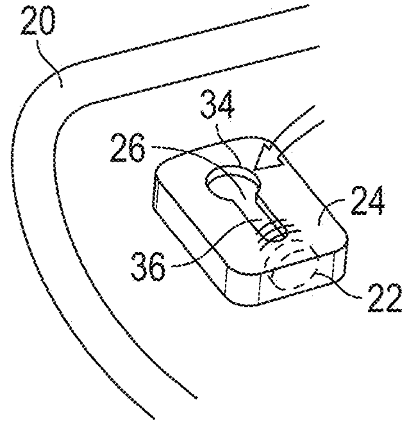
FIGS. 3A-B show another embodiment of a mechanical connector employing magnets in combination with a peg and keyhole connector for connecting and disconnecting a reusable component of a wearable device.
Figure 3B:
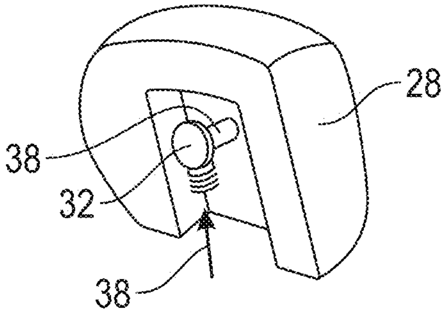

FIGS. 3A-B show another embodiment of a mechanical connector employing magnets in combination with a peg and keyhole connector for connecting and disconnecting a reusable component of a wearable device (such as an external cardiopulmonary physiologic monitor or cardioverter/defibrillator similar to those shown in WO2017/035502) to a disposable component of the wearable device. In this embodiment, the mechanical connector of the disposable component 20 (e.g., an adhesive patient engagement substrate) has a first magnet 22 disposed within a housing 24 having an access keyhole 26. The mechanical connector of the reusable component 28 (e.g., a cardiopulmonary physiologic monitor or defibrillator housing) has a peg 30 with an enlarged end 32 that can fit through the top 34 of access keyhole 26. After insertion of peg 30 into keyhole 26, peg 30 can be moved downward into the slotted portion 36 of keyhole 26 until a second magnet 38 on peg 30 meets and attaches to first magnet 22. There may be multiple mechanical connectors on the disposable component and on the reusable component.

FIGS. 4A-G show embodiments of mechanical connectors 48, 54 for connecting and disconnecting a reusable component 42 (such as cardiopulmonary physiologic monitor or defibrillator housings) of a wearable device (such as an external cardiopulmonary physiologic monitor or cardioverter/defibrillator similar to those shown in WO2017/035502) to a disposable component 44 (such as an adhesive patient engagement substrate) of the wearable device. In this embodiment, the mechanical connectors 48, 54 are male and female mechanical elements. As shown in FIG. 4A, reusable component 42 has four housings 46. A male snap element 48 extends from each housing 46. As shown, the housings 46 may be connected by a flexible connector 50, such as a flexible circuit. Also shown is an optional electrical connector 52. Disposable component 44 has a plurality of female mechanical snap elements 54 in positions corresponding to the positions of male snap elements 48. Disposable component 44 also has an optional electrical connector 56.

FIGS. 4C-E show one embodiment of mechanical snaps that may be used with the wearable device shown in FIGS. 4A-B. In this embodiment, the female snap element 54 has a spring latch 58 and hook side 57 that retains the head 60 of the male snap element inside of female snap element 54 until a sufficient force is applied to remove it (e.g., by peeling), as suggested by FIG. 4E. FIGS. 4F-G show another embodiment of a mechanical snap in which the female snap element 54 has a plurality of cantilever wall sections 62 separated by cutouts 64. Wall sections 62 move radially outward in response to an insertion force applied to the top 66 of the wall section by the head 60 of the male snap element during connection or a retraction force applied to the underside of a projection of the wall section by head 60 during disconnection.

Figure 5A:
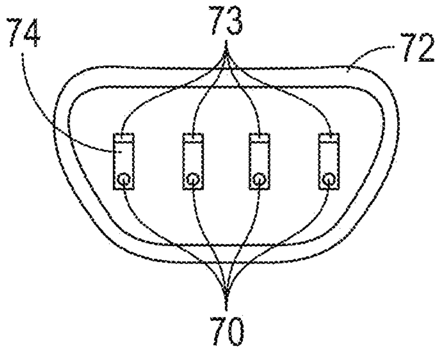
FIGS. 5A-B show an embodiment of a wearable device in which the mechanical connectors of the disposable component are disposed on pivotable bases.
Figure 5B:
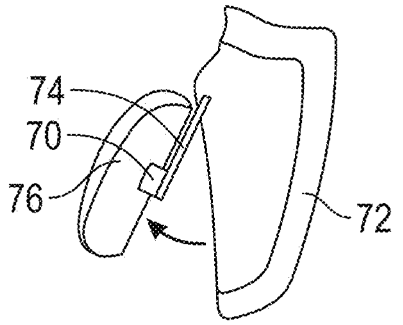

FIGS. 5A-B show a front view and a side view (on body), respectively, of an embodiment of a wearable device (such as an external cardiopulmonary physiologic monitor or cardioverter/defibrillator similar to those shown in WO2017/035502) in which the mechanical connectors 70 (e.g., inter-locks) of the disposable component 72 (such as an adhesive patient engagement substrate) are disposed on pivotable bases 74 with pivot points 73. When the reusable component 76 (such as the cardiopulmonary physiologic monitor or defibrillator housings) are mechanically attached to the disposable component 72 using any of the mechanical connectors disclosed herein, the reusable component can pivot away from the reusable component, thereby providing more movement flexibility while the wearable device is worn by the patient.

Figure 6A:
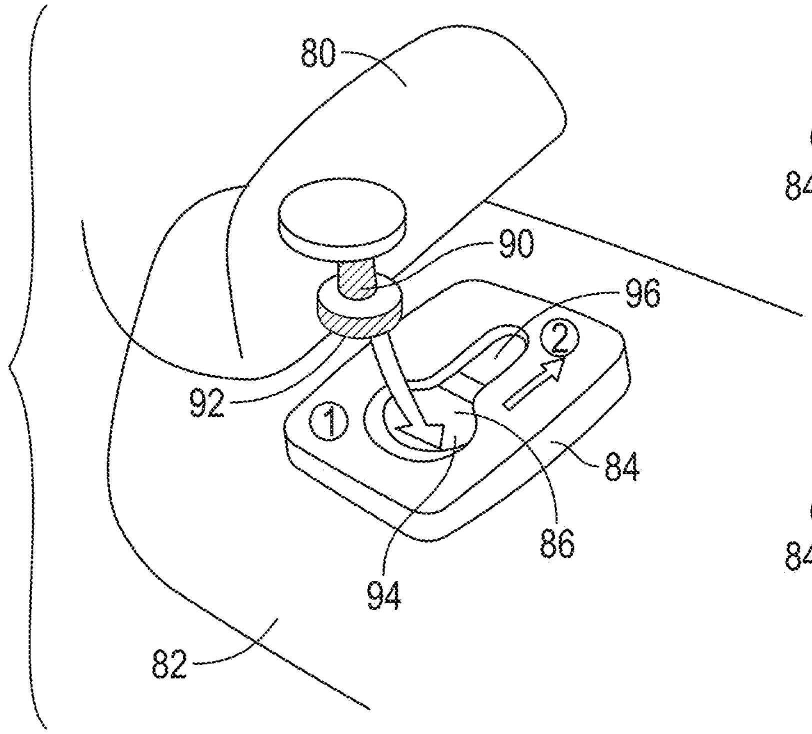
FIGS. 6A-D show embodiments of mechanical connectors for connecting and disconnecting a reusable component of a wearable device to a disposable component of the wearable device.
Figure 6B:
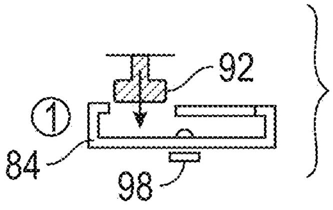
Figure 6C:
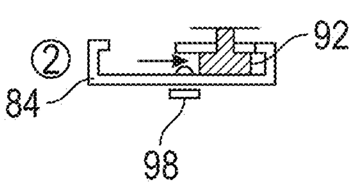
Figure 6D:
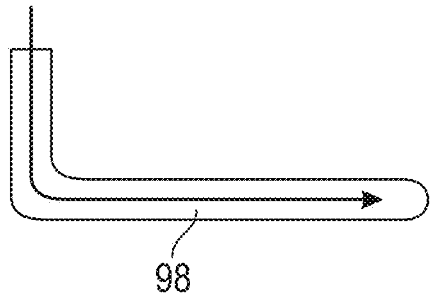

FIGS. 6A-D show embodiments of mechanical connectors for connecting and disconnecting a reusable component 80 (such as cardiopulmonary physiologic monitor or defibrillator housings) of a wearable device (such as an external cardiopulmonary physiologic monitor or cardioverter/defibrillator similar to those shown in WO2017/035502) to a disposable component 82 (such as an adhesive patient engagement substrate) of the wearable device. Similar to the embodiment of FIGS. 3A-B, this embodiment employs a peg and keyhole connector. Housing 84 on the top side of disposable component 82 has an access keyhole 86. The mechanical connector of the reusable component 80 (e.g., a cardiopulmonary physiologic monitor or defibrillator housing) has a peg 90 with an enlarged end 92 that can fit through the top 94 of access keyhole 86. After insertion of peg 90 into keyhole 86, peg 90 can be moved downward into the slotted portion 96 of keyhole 86, and a locking feature (e.g., lock 98) may be engaged to prevent peg 90 from moving back through slot 96, as shown in FIG. 6A-C. There may be multiple mechanical connectors on the disposable component and on the reusable component. In some embodiments, the slotted portion of the keyhole may extend in two or more directions, as shown by the dogleg-shaped slot 98 of FIG. 6D.

Figure 7A:
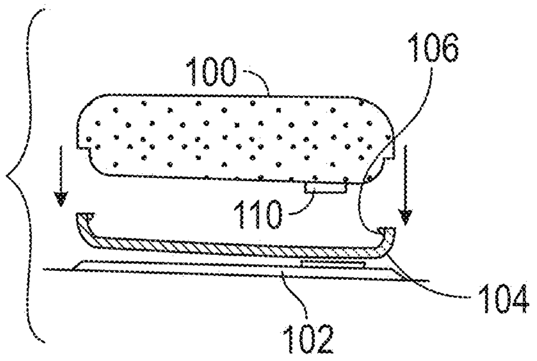
FIGS. 7A-B show embodiments of mechanical connectors for connecting and disconnecting a reusable component of a wearable device to a disposable component of the wearable device.
Figure 7B:
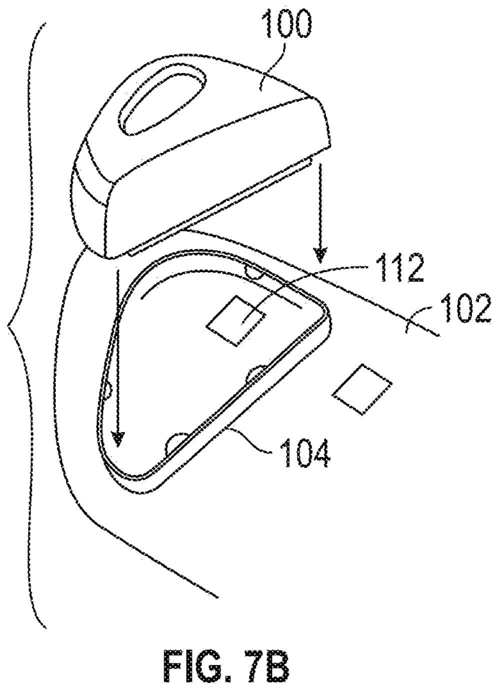

FIGS. 7A-B show an embodiment of mechanical connectors for connecting and disconnecting a reusable component 100 (such as cardiopulmonary physiologic monitor or defibrillator housings) of a wearable device (such as an external cardiopulmonary physiologic monitor or cardioverter/defibrillator similar to those shown in WO2017/035502) to a disposable component 102 (such as an adhesive patient engagement substrate) of the wearable device. In this embodiment, the disposable component mechanical connector is a cradle 104 having an inwardly projecting lip 106 at its open end. A ridge 108 or other outwardly projecting surface on the exterior of reusable component 100 engage lip 106 during insertion and deform cradle 104 sufficiently to snap the reusable component 100 into the cradle. This embodiment may provide a waterproof connection as a mechanical connection that is easier for users to see. Also shown in FIGS. 7A-B are electrical connectors 110 and 112 on the reusable component and disposable component, respectively, that provide electrical communication between the reusable component and the disposable component when the mechanical connection is made.

In an alternative embodiment (not shown), the cradle may have an open end for sliding insertion of the reusable component into the cradle.

Figure 8A:
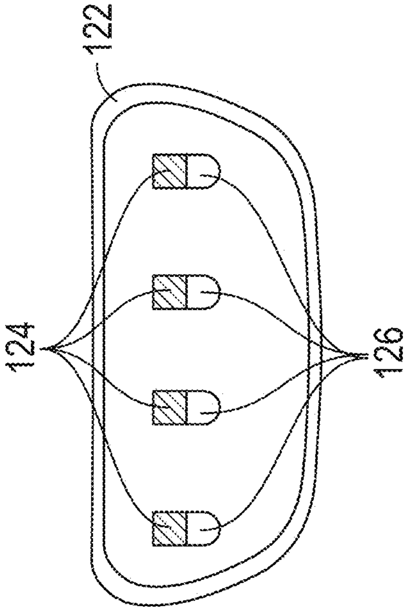
FIGS. 8A-B show embodiments of mechanical connectors for connecting and disconnecting a reusable component of a wearable device to a disposable component of the wearable device.
Figure 8B:
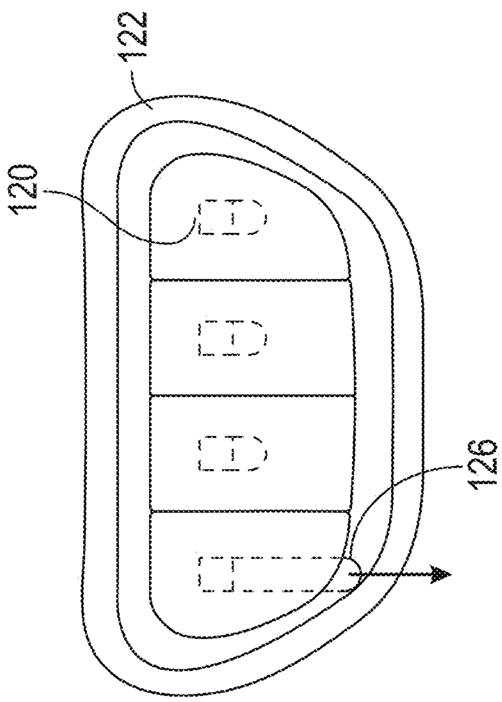

FIGS. 8A-B show front views of an embodiment of mechanical connectors for connecting and disconnecting a reusable component 120 (such as cardiopulmonary physiologic monitor or defibrillator housings) of a wearable device (such as an external cardiopulmonary physiologic monitor or cardioverter/defibrillator similar to those shown in WO2017/035502) to a disposable component 122 (such as an adhesive patient engagement substrate) of the wearable device. In this embodiment, the disposable component mechanical connectors are adhesive areas 124 on the top side of the disposable component 122 that engage the bottom side of the reusable component 120. To disconnect the reusable component 120 from the disposable component 122, one end of the reusable component 120 may be pivoted away from the disposable component to expose pull tabs 126 associated with each adhesive area 124. Pulling down on pull tabs 126, as shown in FIG. 8B, separates the substrates beneath the adhesive areas from the disposable component, thereby allowing the removal of the reusable component from the disposable component.

Figure 9A:
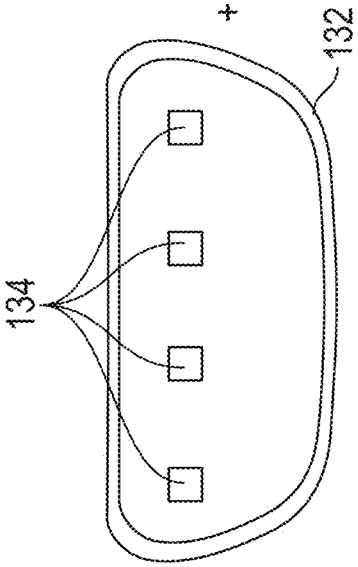
FIGS. 9A-C show embodiments of mechanical connectors for connecting and disconnecting a reusable component of a wearable device to a disposable component of the wearable device.
Figure 9B:
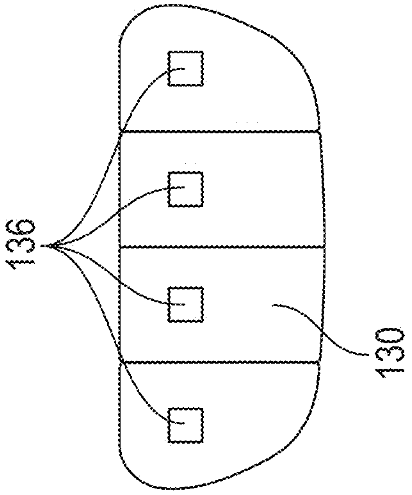
Figure 9C:
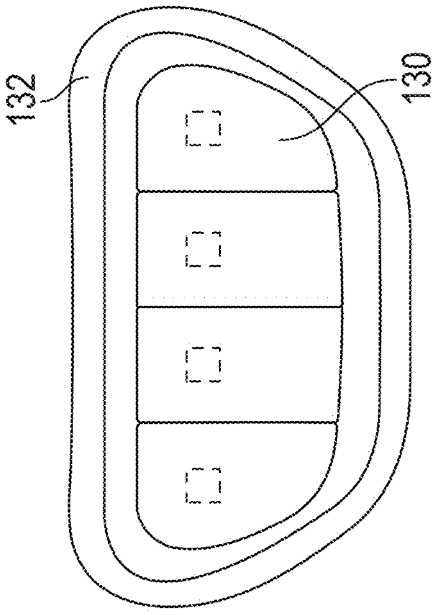

FIGS. 9A-C show an embodiment of mechanical connectors for connecting and disconnecting a reusable component 130 (such as cardiopulmonary physiologic monitor or defibrillator housings) of a wearable device (such as an external cardiopulmonary physiologic monitor or cardioverter/defibrillator similar to those shown in WO2017/035502) to a disposable component 132 (such as an adhesive patient engagement substrate) of the wearable device. FIGS. 9A and 9C show front views; and FIG. 9B shows a back view. This embodiment employs hook and loop connectors 134 and 136 (such as Velcro® material) on the top of the disposable component 132 and the bottom of the reusable component 130, respectively, to attach and detach the disposable component from the reusable component.

FIGS. 10A-C show an embodiment of mechanical connectors for connecting and disconnecting a reusable component 140 (such as cardiopulmonary physiologic monitor or defibrillator housings) of a wearable device (such as an external cardiopulmonary physiologic monitor or cardioverter/defibrillator similar to those shown in WO2017/035502) to a disposable component 142 (such as an adhesive patient engagement substrate) of the wearable device. In this embodiment, the reusable component mechanical connector has a post 144 with an elongated foot 146. The disposable component mechanical connector has a rotatable housing 148 with an opening 150 shaped just larger than the foot 146. After insertion of the foot 146 through opening 150 into housing 148, a tab 152 extending from the housing 148 may be used to rotate housing 148 to change the orientation of opening 150 with respect to foot 146, thereby preventing post 144 from being withdrawn from housing 148. To disconnect the reusable component 140 from the disposable component 142, tab may be used to rotate housing 148 to line up opening 150 with foot 146, thereby permitting post 146 to be withdrawn from housing 148.

Figure 11A:
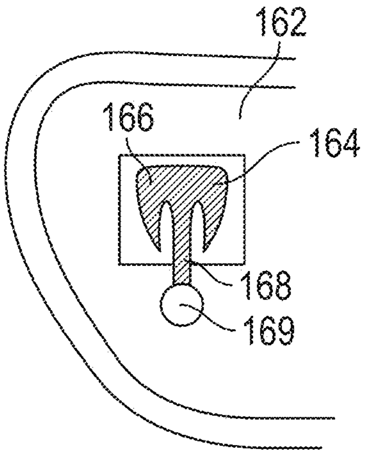
FIGS. 11A-E show embodiments of mechanical connectors for connecting and disconnecting a reusable component of a wearable device to a disposable component of the wearable device.
Figure 11B:
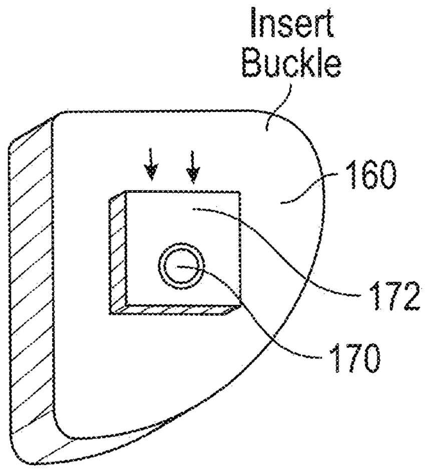
Figure 11C:
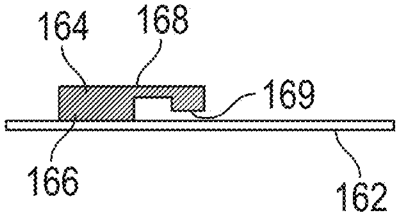
Figure 11D:
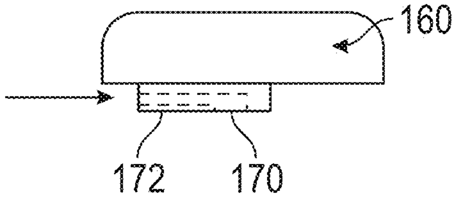
Figure 11E:
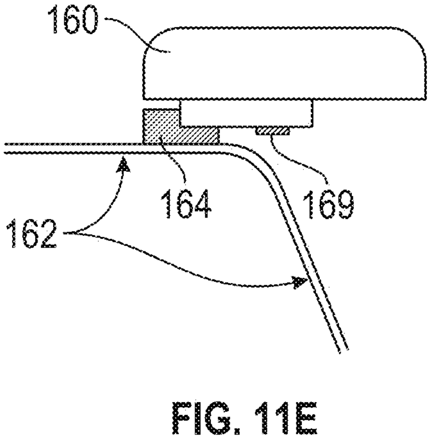

FIGS. 11A-E show an embodiment of mechanical connectors for connecting and disconnecting a reusable component 160 (such as cardiopulmonary physiologic monitor or defibrillator housings) of a wearable device (such as an external cardiopulmonary physiologic monitor or cardioverter/defibrillator similar to those shown in WO2017/035502) to a disposable component 162 (such as an adhesive patient engagement substrate) of the wearable device. FIGS. 11A and 11B show front and back views, respectively; and FIGS. 11C-11D show a side view, with FIG. 11E showing a side view mated. In this embodiment, the disposable component mechanical connector is a buckle 164 attached at one end 166 to the top side of the disposable component. A prong 168 extends in a cantilever manner from the buckle's attached end 166, and a raised element 169 projects downwardly toward the top side of the disposable component. The reusable component mechanical connector has an opening 170 in a plate 172 disposed above the bottom side of the reusable component 160. To mechanically connect the reusable component to the disposable component, the prong 168 is inserted between the plate 172 and the bottom side of the reusable component as indicated in FIG. 11D. The distance between the plate 172 and the bottom surface of the reusable component 160 is slightly greater than the distance between the bottom surface of raised element 169 and the top side of the disposable component, which cause prong 168 to bend upward as it is inserted between plate 172 and the bottom surface of the reusable component until the raised element 169 of the prong 168 goes into, and protrudes through, opening 170, thereby mechanically locking the reusable component to the disposable component. To detach the reusable component from the disposable component, the disposable component may be bent to expose the buckle release mechanism or portion of the raised element protruding through opening 170, as shown in FIG. 11E, and the raised element may be pushed or squeezed out of opening 170 to release the reusable component from the disposable component.

In another embodiment, the buckle of the disposable component mechanical connector may have one or more cantilevered elements extending laterally through one or more openings in the reusable component mechanical connector.

In some embodiments, the reusable component will have a plurality of housings, and there will be at least one mechanical connection between each housing and the disposable component. These mechanical connections could be spread evenly across the wearable device. Other embodiments will employ fewer mechanical connections. Furthermore, some mechanical connections may be stronger (e.g., to support the weight of the reusable portion) and some mechanical connections may be weaker (e.g., more for alignment and registration and less for supporting weight).

Figure 12:
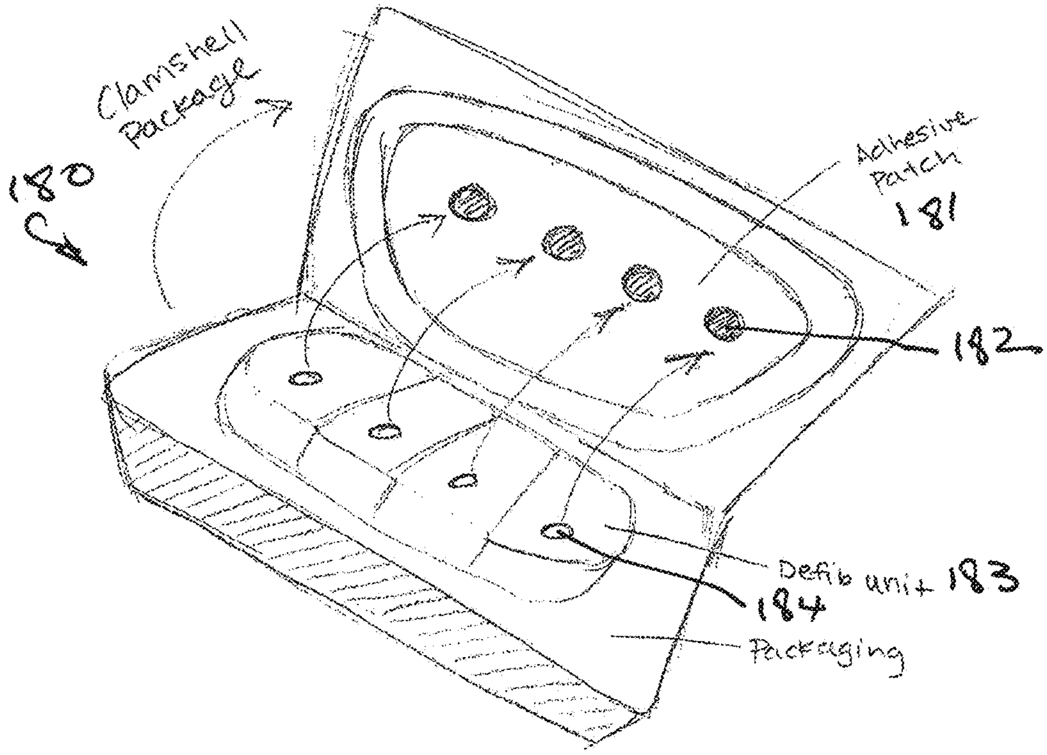
FIG. 12 shows a tool for aligning the disposable component mechanical connectors with the reusable component mechanical connectors.

FIG. 12 shows a tool 180 for aligning the disposable component mechanical connectors 182 with the reusable component mechanical connectors 184. Tool 180 is a hinged container holding the disposable component 181 in proper alignment with the reusable component 183 so that when the lid 186 is closed, the mechanical connectors attach to each other.

Figure 33A:
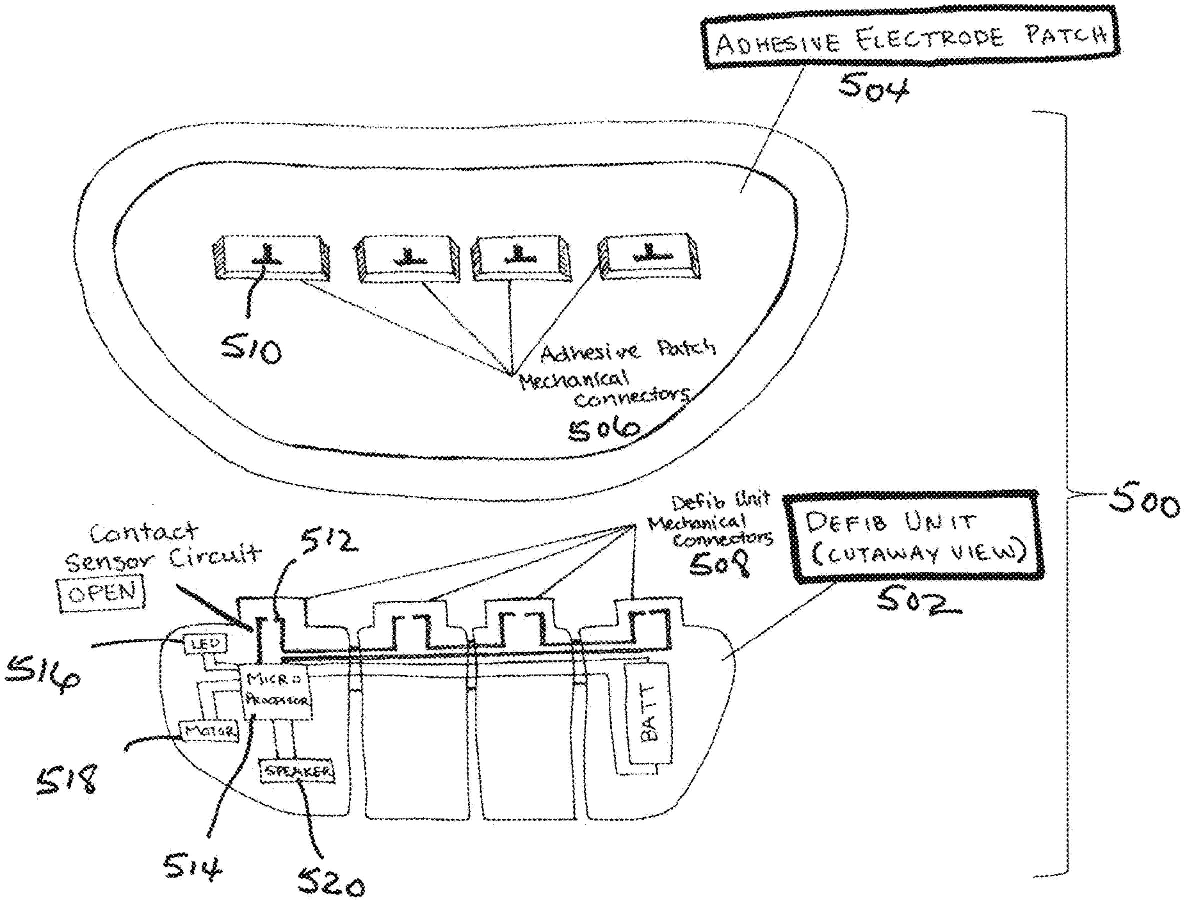
FIGS. 33A-B show a wearable device with a reusable component and a disposable component.
Figure 33B:
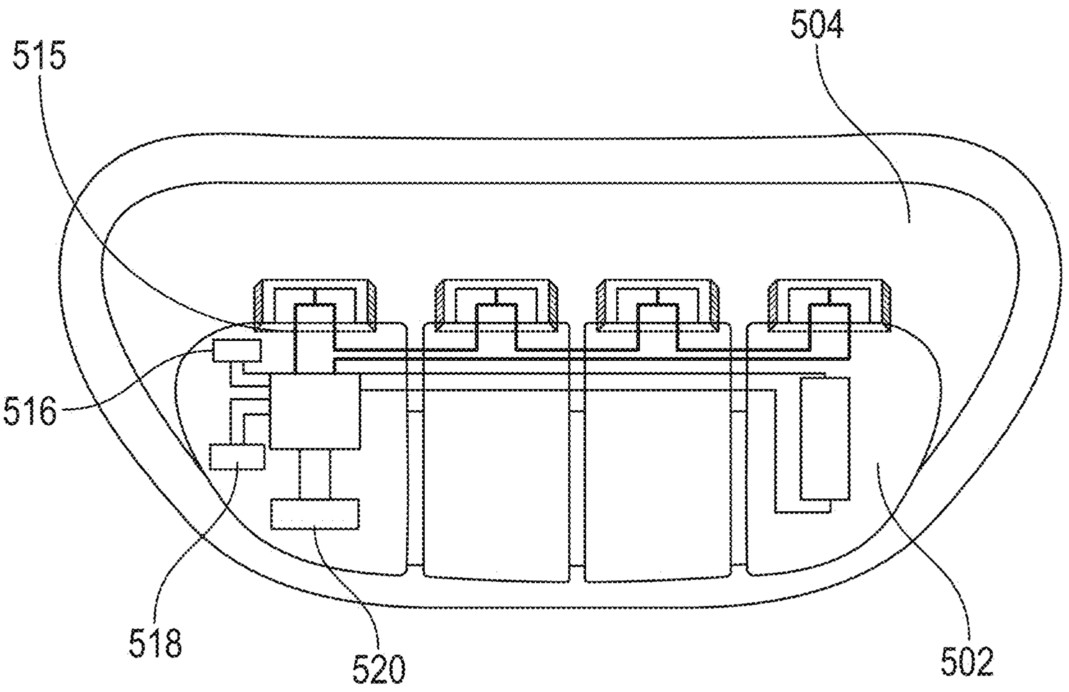

In addition to the snapping sound or other audible indication of a successful mechanical connection between the disposable component and the reusable component, some embodiments provide an electronically-generated feedback of successful mechanical connection, such as an indicator light, vibration or generated sound. FIGS. 33A-B show a wearable device 500 (such as a cardiopulmonary physiologic monitor or an external cardioverter/defibrillator similar to those shown in WO2017/035502) with a reusable component 502 (such as cardiopulmonary physiologic monitor or defibrillator housings) and a disposable component 504 (such as an adhesive patient engagement substrate). The disposable component 504 has mechanical connectors 506 that connect to corresponding mechanical connectors 508 on the reusable component 502. Each mechanical connector 506 on the disposable component 504 has a conductive element 510 that contact one or more conductive elements 512 in each of the reusable component mechanical connectors 508 to close a circuit 512 leading to a microprocessor 514 in the reusable component. When the microprocessor 514 detects that the circuit 512 is closed, it announces the successful mechanical connection between all of the mechanical connectors 506 with their corresponding mechanical connectors 508 by lighting one or more lights 516, vibrating a motor 518 and/or emitting a sound via a speaker 520. A contact sensor 515 can be used to detect status of the circuit 512, shown open in FIG. 33A and closed in FIG. 33B.

Figure 13:
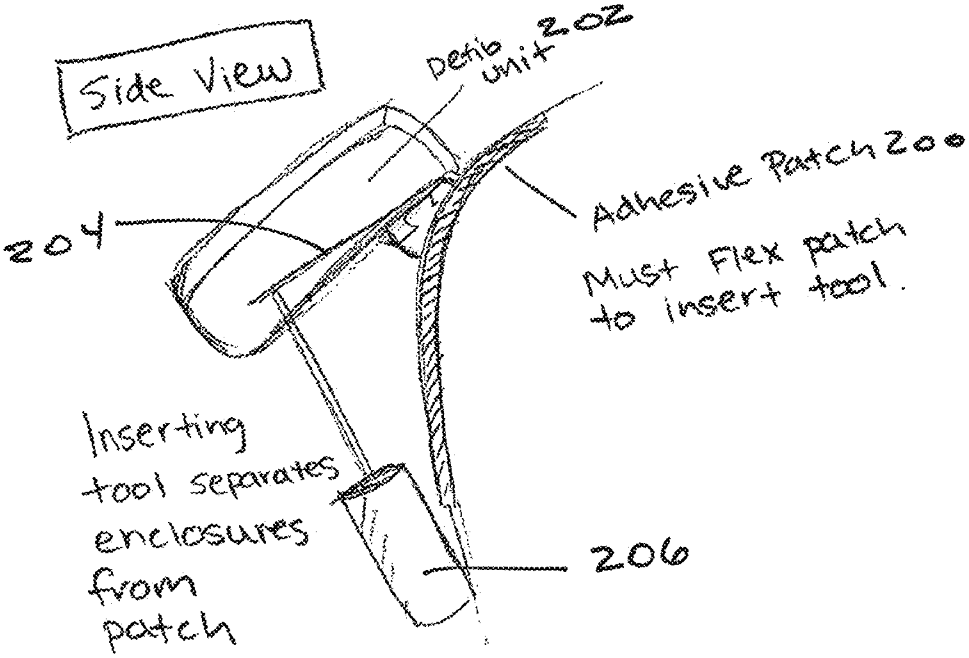
FIG. 13 shows an embodiment of a wearable device in which the disposable component includes an adhesive patient engagement substrate and the reusable component includes a cardiopulmonary physiologic monitor or defibrillator housing.

In embodiments of the wearable device where the disposable component includes an adhesive patient engagement substrate, disconnection of the disposable component mechanical connector from the reusable component mechanical connector may not be possible while the patient engagement substrate is adhered to the patient. This feature helps ensure that the disposable and reusable components are connected while the wearable device is being worn. For example, FIG. 13 shows an embodiment of the wearable device in which the disposable component includes an adhesive patient engagement substrate 200 and the reusable component includes a cardiopulmonary physiologic monitor or defibrillator housing 202. In order to access the mechanical connectors 204 with a tool 206, the patient engagement substrate 200 must be bent more than it could be bent while adhesively attached to the patient.

Figure 14A:
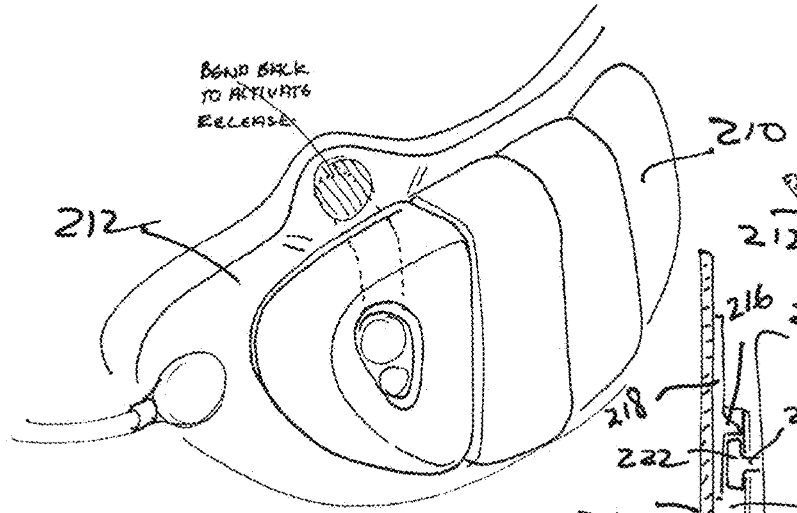
FIGS. 14A-C show embodiments of mechanical connectors for connecting and disconnecting a reusable component of a wearable device to a disposable component of the wearable device.
Figure 14B:
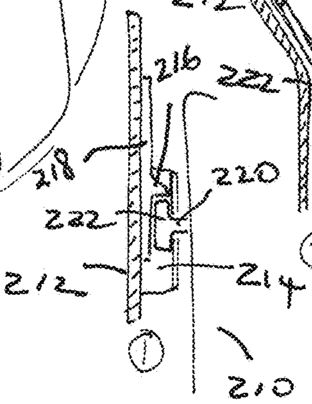
Figure 14C:
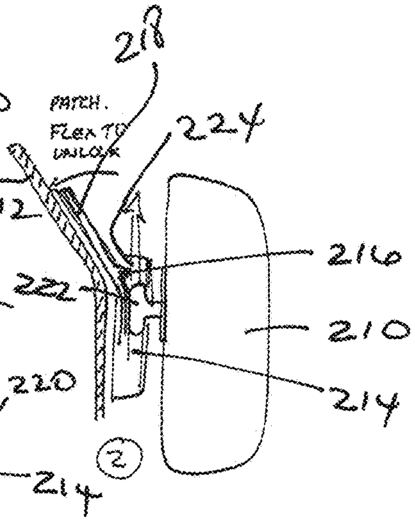

FIGS. 14A-C show an embodiment of mechanical connectors for connecting and disconnecting a reusable component 210 (such as cardiopulmonary physiologic monitor or defibrillator housings) of a wearable device (such as an external cardiopulmonary physiologic monitor or cardioverter/defibrillator similar to those shown in WO2017/035502) to a disposable component (such as an adhesive patient engagement substrate 212) of the wearable device. In this embodiment, the disposable component mechanical connector includes a slot 214 on the top side of the substrate 212 and a tab 216 extending from a bendable plate 218 on the substrate (or, alternatively, extending directly from the patient engagement substrate with no intervening plate). The reusable component mechanical connector has a peg 220 with an enlarged end 222 that can be moved into slot 214 from an open end 224 of the slot to connect the mechanical connectors. When the patient engagement substrate 212 and bendable plate 218 are unbent, the tab 216 prevents the enlarged end 222 of peg 220 from leaving the slot 214, as shown in FIG. 14B. When the patient engagement substrate 212 and bendable plate 218 are bent, however, tab 216 moves away from the enlarged end of the peg, enabling it to be removed from the slot 214, thereby disconnecting the cardiopulmonary physiologic monitor or defibrillator housing from the patient engagement substrate, as shown in FIG. 14C.

Figure 35A:
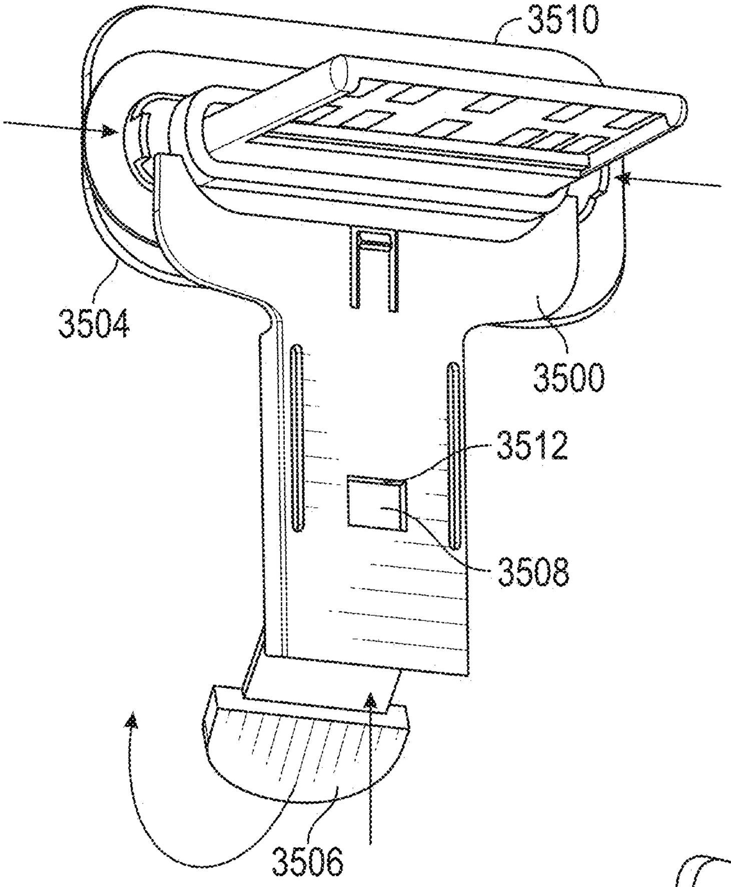
FIGS. 35A-B show an embodiment of a trigger prevention mechanism for preventing disconnection of a reusable component of a wearable device from a disposable component of the wearable device while the device is being worn.
Figure 35B:
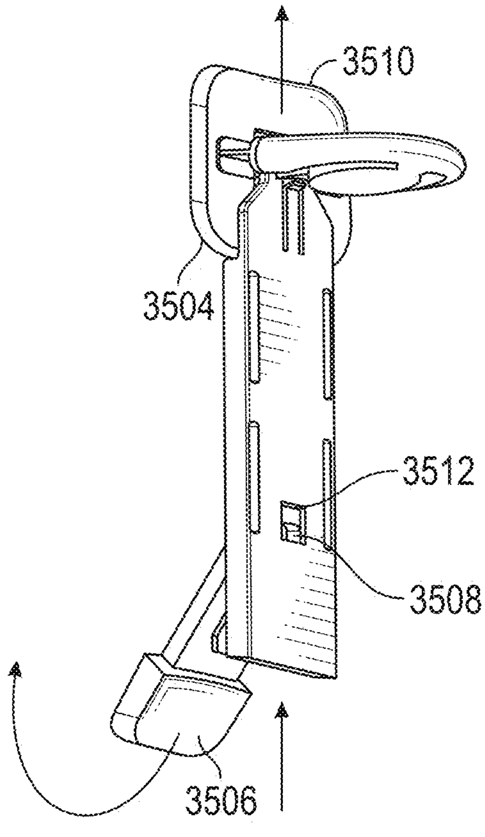

FIGS. 35A-B show an embodiment of mechanical connectors for connecting and disconnecting a reusable component (such as cardiopulmonary physiologic monitor or defibrillator housings) of a wearable device (such as an external cardiopulmonary physiologic monitor or cardioverter/defibrillator similar to those shown in WO2017/035502) to a disposable component (such as an adhesive patient engagement substrate) of the wearable device. In this embodiment, the disposable component mechanical connector includes a plate 3504 comprising a bendable portion 3506 at one end of the plate, a protrusion 3508 in a mid section of the plate 3504, and a locking mechanism (e.g., spring lock, detent, etc.) at another portion of the plate 3510. In some embodiments, the protrusion and lock may be positioned directly on the patient engagement substrate with no intervening plate. The protrusion 3508 is configured to interact with an aperture 3512 in a portion of the reusable component mechanical connector. To unlock the connectors, the bendable portion 3506 of the disposable component mechanical connector is bent backwards, away from the reusable component mechanical connector. The reusable component mechanical connector can then be slid along a length of the disposable component mechanical connector, unlocking the locking mechanism. It will be appreciated that, in some embodiments, the disposable component mechanical connector can instead be slide along a length of the reusable component mechanical connector. FIG. 35B shows another embodiment of a disposable component mechanical connector including a plate 3504 comprising a bendable portion 3506 at one end of the plate, a protrusion 3508 in a mid section of the plate 3504, and a spring lock 3512 at another portion of the plate. Upon bending back the bendable portion 3506, the protrusion 3508 disengages from aperture 3512 in the reusable component mechanical connector. The plate 3510 can then be slid along a length of the disposable component mechanical connector, disengaging spring lock 3512.

Figure 15A:
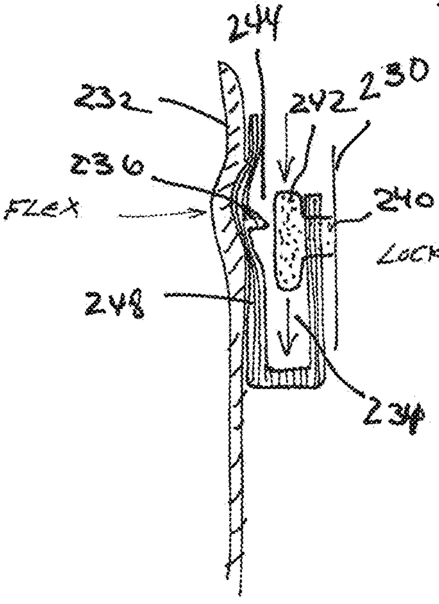
FIGS. 15A-C show embodiments of mechanical connectors for connecting and disconnecting a reusable component of a wearable device to a disposable component of the wearable device.
Figure 15B:
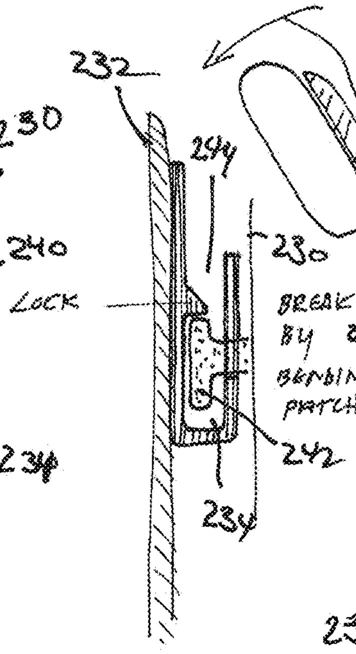
Figure 15C:
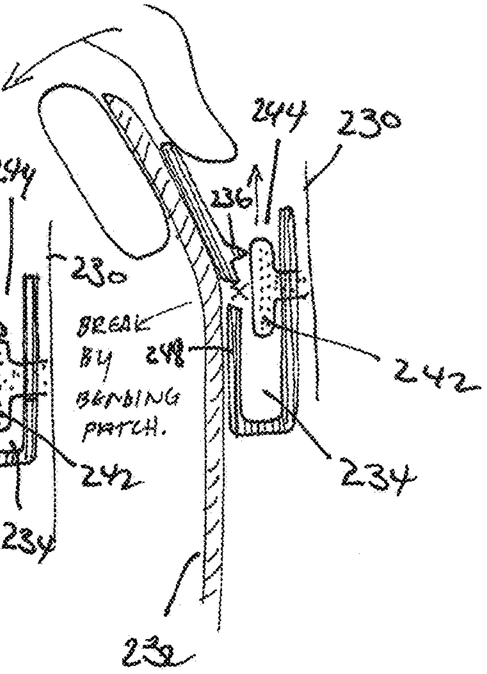

FIGS. 15A-C show an embodiment of mechanical connectors for connecting and disconnecting a reusable component 230 (such as cardiopulmonary physiologic monitor or defibrillator housings) of a wearable device (such as an external cardioverter/defibrillator similar to those shown in WO2017/035502) to a disposable component (such as an adhesive patient engagement substrate 232) of the wearable device. In this embodiment, the disposable component mechanical connector includes a slot 234 on the top side of the substrate 232 and a tab 236 extending from a plate 248 on the substrate. The reusable component mechanical connector has a peg 240 with an enlarged end 242 that can be moved into slot 234 from an open end 244 of the slot to connect the mechanical connectors. Advancement of the enlarged portion of the peg into the slot causes the plate 248 to flex to move the tab 236 back, thereby permitting the enlarged end 242 of peg 240 to move into slot. When the patient engagement substrate 232 and plate 248 return to their unbent state, the tab 236 prevents the enlarged end 242 of peg 240 from leaving the slot 234, as shown in FIG. 15B. To disconnect the reusable component from the patient engagement substrate, however, the substrate 232 and plate 248 are bent until the plate breaks, as shown in FIG. 15C, thereby permitting tab 236 to move away from the enlarged end of the peg and enabling it to be removed from the slot 234, thereby disconnecting the cardiopulmonary physiologic monitor or defibrillator housing from the patient engagement substrate.

In other embodiments in which the disposable component of the wearable device includes a patient engagement substrate, perforations or seams in the patient engagement substrate may permit the user to tear the substrate to disconnect the reusable component from the substrate.

Another aspect of the invention is the manner in which reusable component(s) of a wearable device may be electrically connected to, and disconnected from, disposable component(s). Embodiments of the invention provide robust, waterproof, simple to operate (even for patients with low dexterity), reliable electrical connections between the reusable component of a wearable device (such as, e.g., an external cardiopulmonary physiologic monitor or cardioverter/defibrillator similar to those shown in WO2017/035502) and a disposable component of that device (such as, e.g., an adhesively attachable patient engagement substrate and/or a battery). In many of the embodiments, the reusable component can be electrically disconnected from the disposable component only when the wearable device is not being worn by the patient. The electrical connection mechanisms described herein can be used in combination with each other and with any of the embodiments described in this disclosure.

Figure 16A:
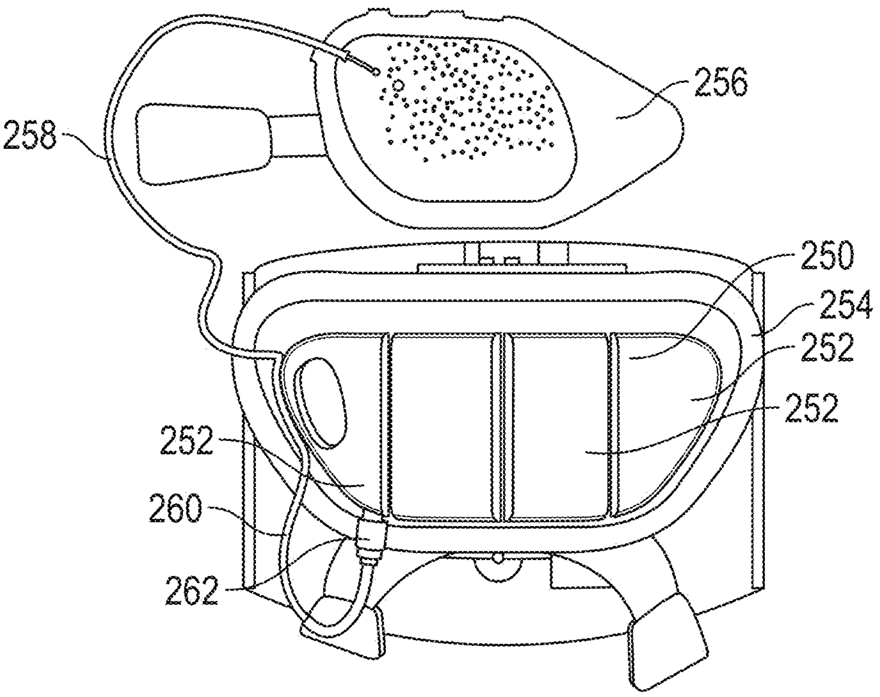
FIGS. 16A-C show an embodiment of electrical connectors for electrically connecting and disconnecting a reusable component of a wearable device to a disposable component of the wearable device.
Figure 16B:
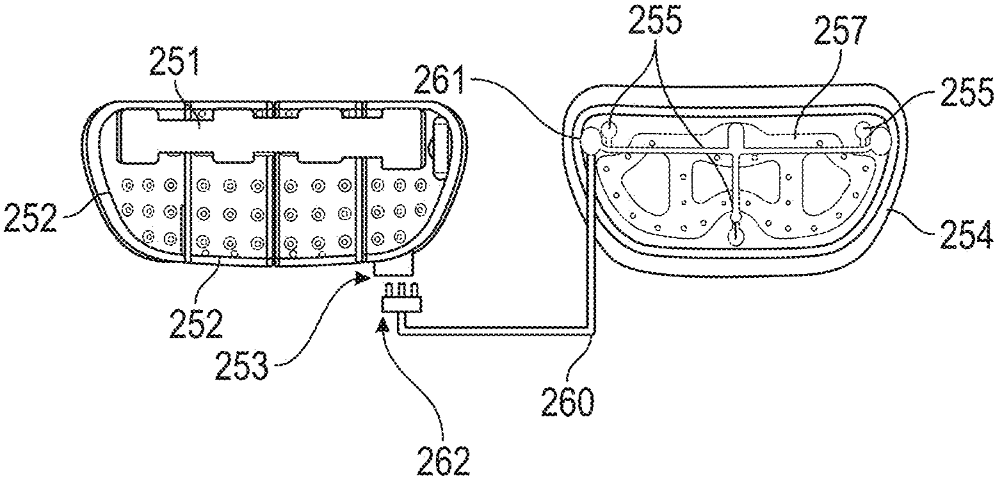
Figure 16C:
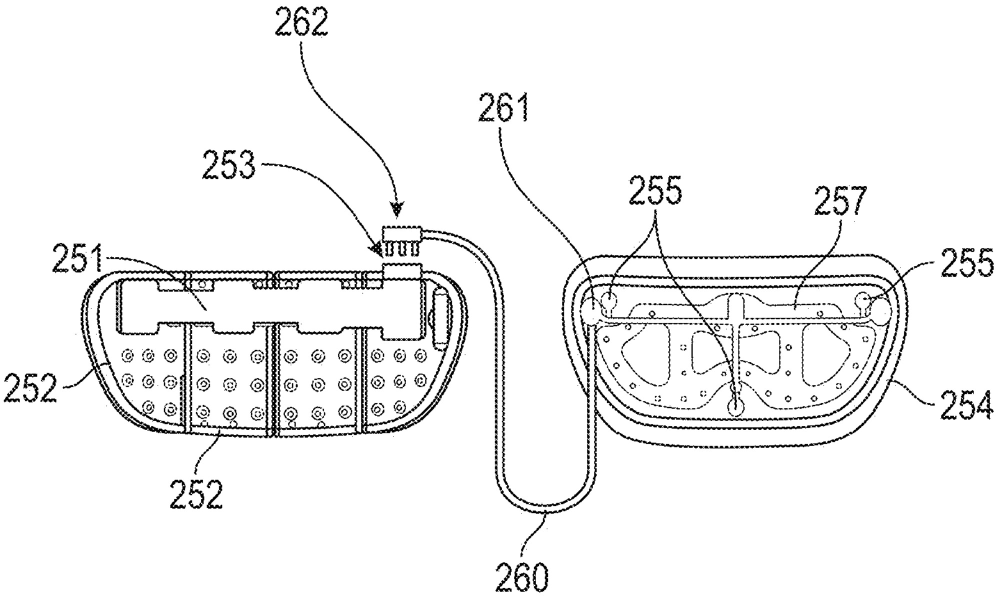

FIGS. 16A-B show an embodiment of electrical connectors for electrically connecting and disconnecting a reusable component 250 (such as electronic cardiopulmonary physiologic monitor or defibrillator components within housings 252) of a wearable device to a disposable component (such as first and second adhesive patient engagement substrates 254 and 256) of the wearable device. In this embodiment, a first cable 258 extends from first patient engagement substrate 254 to the second patient engagement substrate 256, and a second cable 260 extends from a flexible circuit 261 in the first patient engagement substrate 254 to an electrical connector 262. The cable 260 can be connected to the flexible circuit 261 permanently or flex circuit 261 extension. Electrical connector 262 may be connected and disconnected from a mating electrical connector 253 in housing 252 of the reusable component 250. In other words, the cable can plug into the reusable component. Cables 258 and 260 electrically connect the cardiopulmonary physiologic monitor or defibrillator components within housings 252 to electrodes 255, 257 on the bottom side of patient engagement substrates 254 and 256, allowing for sensing of cardiac activity (such as, e.g., ECG signals) or, in the case of a defibrillator, delivery of electric shocks from electrodes on the bottom sides of patient engagement substrates 254 and 256. Electrodes 255 can be ECG electrodes and electrode 257 can be a defibrillator electrode. A flexible circuit 251 provides electrical communication among the cardiopulmonary physiologic monitor or defibrillator components within housings 252. In an alternative embodiment, shown in FIG. 16C, the electrical connector 262 may connect to a corresponding electrical connector 253 integrated into the flexible circuit 251.

Figure 17A:
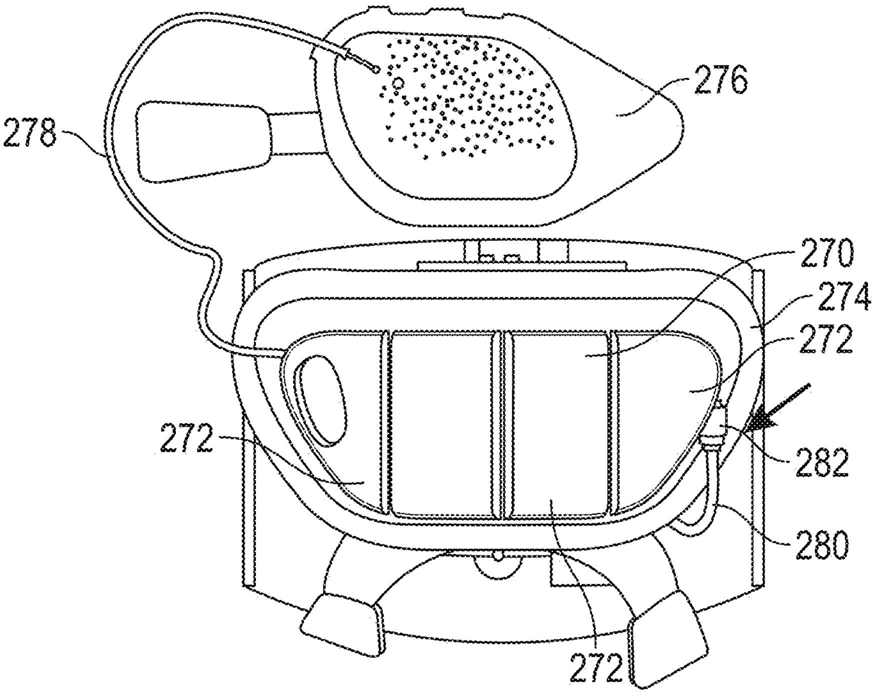
FIGS. 17A-C show an embodiment of electrical connectors for electrically connecting and disconnecting a reusable component of a wearable device to a disposable component of the wearable device.
Figure 17B:
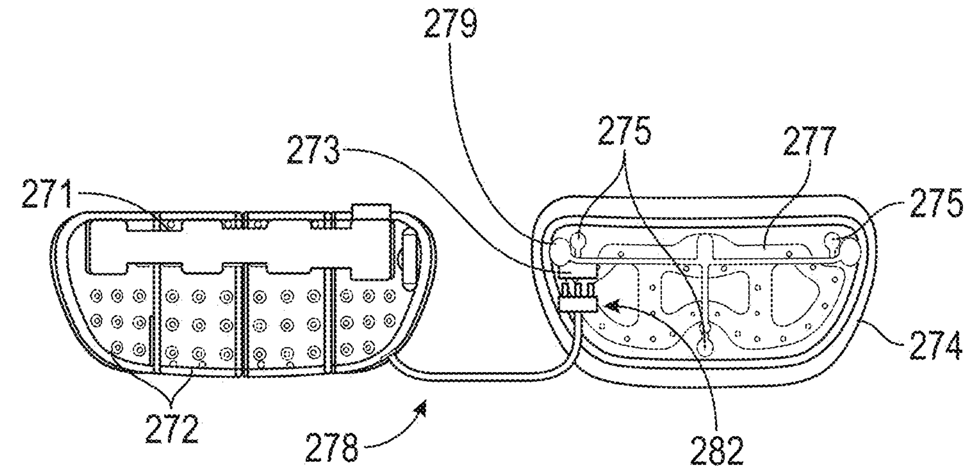
Figure 17C:
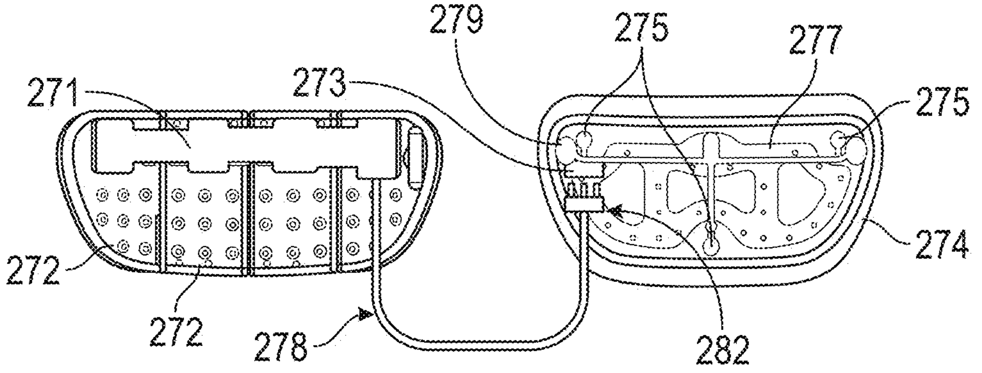

FIGS. 17A-B show an embodiment of electrical connectors for electrically connecting and disconnecting a reusable component 270 (such as electronic cardiopulmonary physiologic monitor or defibrillator components within housings 272) of a wearable device to a disposable component (such as first and second adhesive patient engagement substrates 274 and 276) of the wearable device. In this embodiment, a first cable 278 extends from first patient engagement substrate 274 to the second patient engagement substrate 276, and a second cable 280 extends from one of the cardiopulmonary physiologic monitor or defibrillator housings 272 to an electrical connector 282. The cable 278 can be a cable or additional flex circuit permanently connected to the reusable component 270. Electrical connector 282 may be connected and disconnected from a mating electrical connector 273 extending from or integrated into a flexible circuit 279 in the first patient engagement substrate 274. In other words, the cable can plug into the patient engagement substrate. Cables 278 and 280 electrically connect the cardiopulmonary physiologic monitor or defibrillator components within housings 272 to electrodes 275, 277 on the bottom side of patient engagement substrates 274 and 276, allowing for sensing of cardiac activity (such as, e.g., ECG signals) or, in the case of a defibrillator, delivery of electric shocks from electrodes on the bottom sides of patient engagement substrates 274 and 276. Electrodes 275 can be ECG electrodes; and electrode 277 can be a defibrillator electrode. A flexible circuit 271 provides electrical communication among the cardiopulmonary physiologic monitor or defibrillator components within housings 272. In an alternative embodiment, shown in FIG. 17C, the second cable 280 may extend from the flexible circuit 271 instead of from one of the housings 272.

Figure 18A:
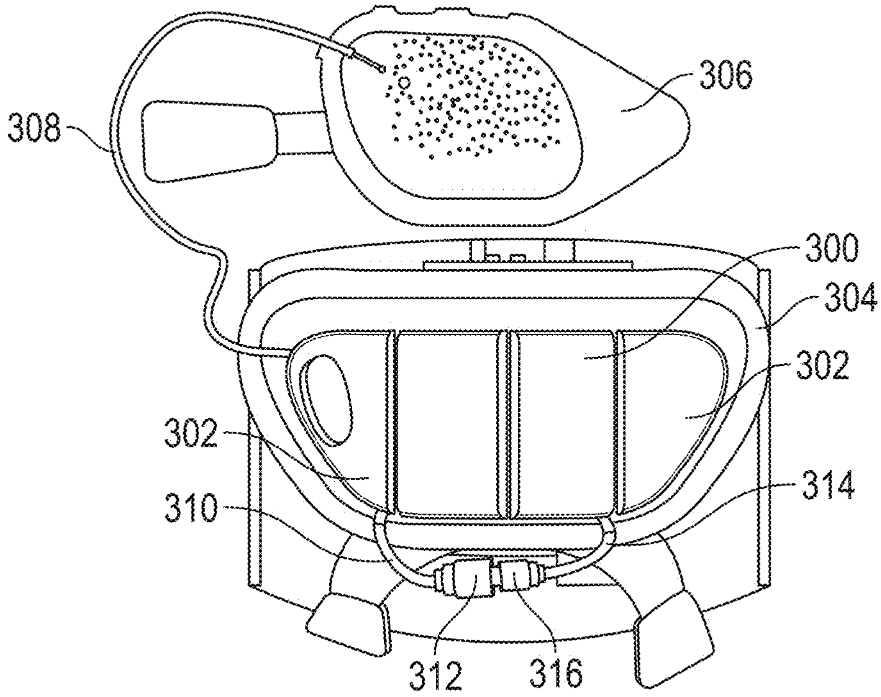
FIGS. 18A-C show embodiments of electrical connectors for electrically connecting and disconnecting a reusable component of a wearable device to a disposable component of the wearable device.
Figure 18B:
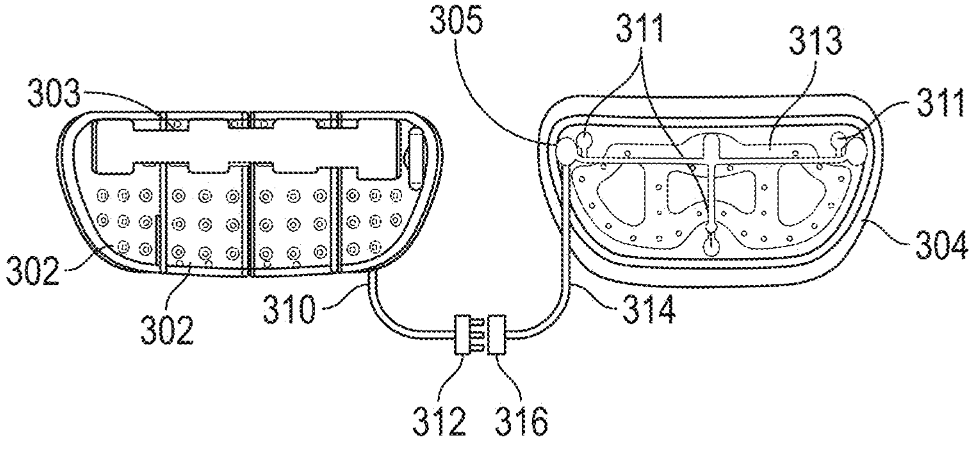
Figure 18C:
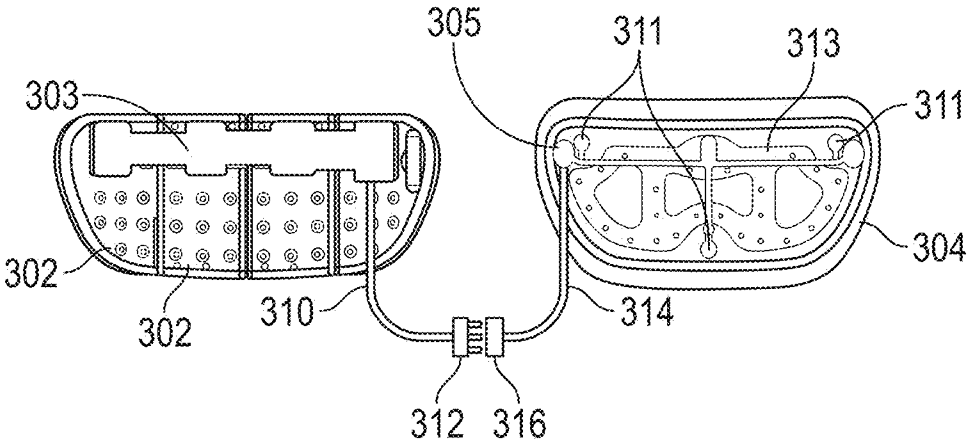

FIGS. 18A-B show an embodiment of electrical connectors for electrically connecting and disconnecting a reusable component 300 (such as electronic cardiopulmonary physiologic monitor or defibrillator components within housings 302) of a wearable device to a disposable component (such as first and second adhesive patient engagement substrates 304 and 306) of the wearable device. In this embodiment, a first cable 308 extends from first patient engagement substrate 304 to the second patient engagement substrate 306, a second cable 310 extends from one of the cardiopulmonary physiologic monitor or defibrillator housings 302 to a first electrical connector 312, and a third cable 314 extends from a flexible circuit 305 of patient engagement substrate 304 to a second electrical connector 316 configured to electrically connect to, and disconnect from, the first electrical connector 312, as shown. Cable 310 can be a cable or an additional flex circuit connected to the reusable component 300. Cable 314 can be a cable or an extension of flex circuit 305. Cables 308, 310 and 314 electrically connect the cardiopulmonary physiologic monitor or defibrillator components within housings 302 to electrodes 311, 313 on the bottom side of patient engagement substrates 304 and 306, allowing for sensing of cardiac activity (such as, e.g., ECG signals) or, in the case of a defibrillator, delivery of electric shocks from electrodes on the bottom sides of patient engagement substrates 304 and 306. Electrodes 311 can be ECG electrodes; and electrode 313 can be a defibrillation electrode. A flexible circuit 303 provides electrical communication among the cardiopulmonary physiologic monitor or defibrillator components within housings 302. In an alternative embodiment, shown in FIG. 18C, the second cable 310 may extend from the flexible circuit 303 instead of from one of the housings 302.

Figure 19A:
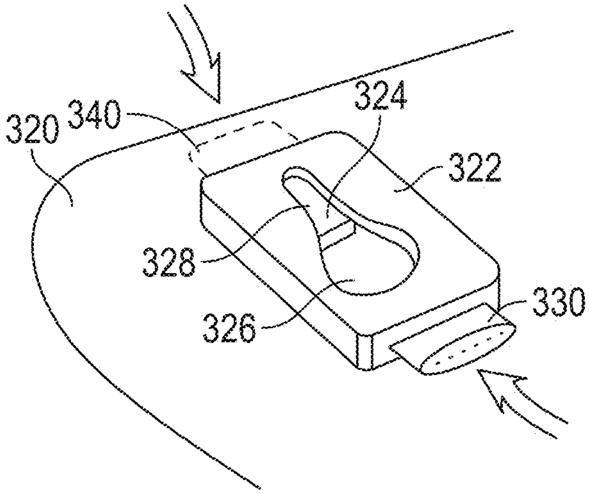
FIGS. 19A-D show an embodiment of a combined electrical and mechanical connector.
Figure 19C:
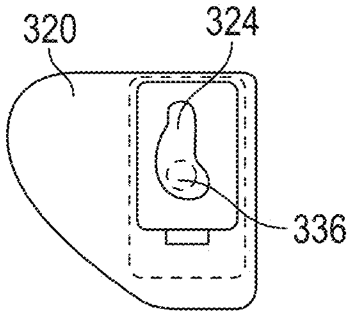
Figure 19D:
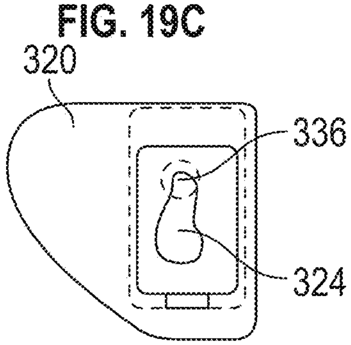
Figure 19B:
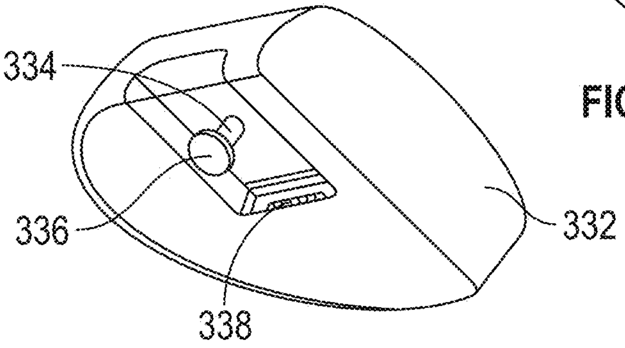

In some embodiments, the mechanical and electrical connectors connecting the reusable component to, and disconnecting the reusable component from, the disposable component are integrated so that the electrical connection occurs simultaneously with the mechanical connection. FIGS. 19A-D show one embodiment of a combined electrical and mechanical connector. In FIG. 19A, mounted on the top side of the wearable device's disposable component (e.g., an adhesive patient engagement substrate 320) is a mechanical connector housing 322 having a keyhole opening 324 with a wide portion 326 above a narrow portion 328. An electrical connector 330 extends from a side of the housing 322 adjacent to the wide portion 326 of the keyhole opening 324. The corresponding structure on the reusable component of the wearable device (e.g., a housing 332 of a cardiopulmonary physiologic monitor or a cardioverter/defibrillator similar to those shown in WO2017/035502) is a peg 334 having an enlarged end 336 to form the mechanical connector of the reusable component. The reusable component's electrical connector 338 is shown adjacent to peg 334. To connect the reusable component mechanically and electrically to the disposable component, the enlarged end 336 of peg 334 is inserted into the wide portion 326 of keyhole opening 324, as shown in FIG. 19C. The peg 334 is then advanced in keyhole opening 324 until the enlarged end 336 is beneath the narrow portion 328 of the keyhole opening such that the peg can no longer be withdrawn from housing 322, thereby mechanically connecting the reusable component to the disposable component. When peg 334 reaches the limit of its travel within keyhole opening 324, as shown in FIG. 19D. the reusable component's electrical connector 338 will engage the disposable component's electrical connector 330 to electrically connect the reusable component to the disposable component. To disconnect the reusable component from the disposable component, a movable disconnection actuator 340 may be depressed to move peg 334 to the wide portion 326 of keyhole opening 324 to disconnect the electrical connectors 330 and 338 and to permit the enlarged end 336 of the peg to be removed from the keyhole opening 324.

Figure 20:
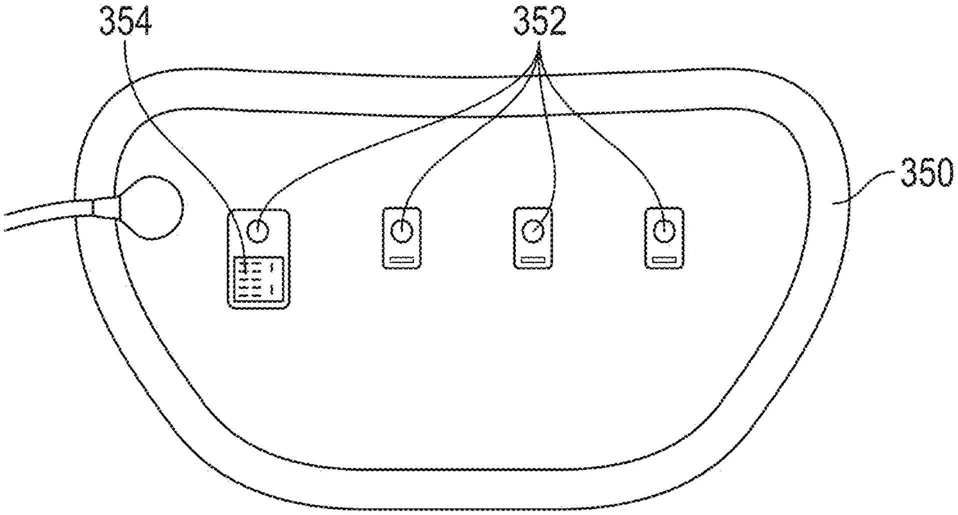
FIG. 20 shows an embodiment of a wearable device's disposable component with four mechanical connectors and an electrical connector.

FIG. 20 shows an embodiment of a wearable device's disposable component (such as, e.g., an adhesive patient engagement substrate 350) with four mechanical connectors 352 (such as, e.g., the snap connectors described above) and an electrical connector 354. When the wearable device's reusable component (e.g., housings containing cardiopulmonary physiologic monitor or cardioverter/defibrillator similar to those shown in WO2017/035502 components) are mechanically attached to mechanical connectors 352, the reusable component's electrical connector will automatically connect to electrical connector 354 at the same time.

Figure 21:
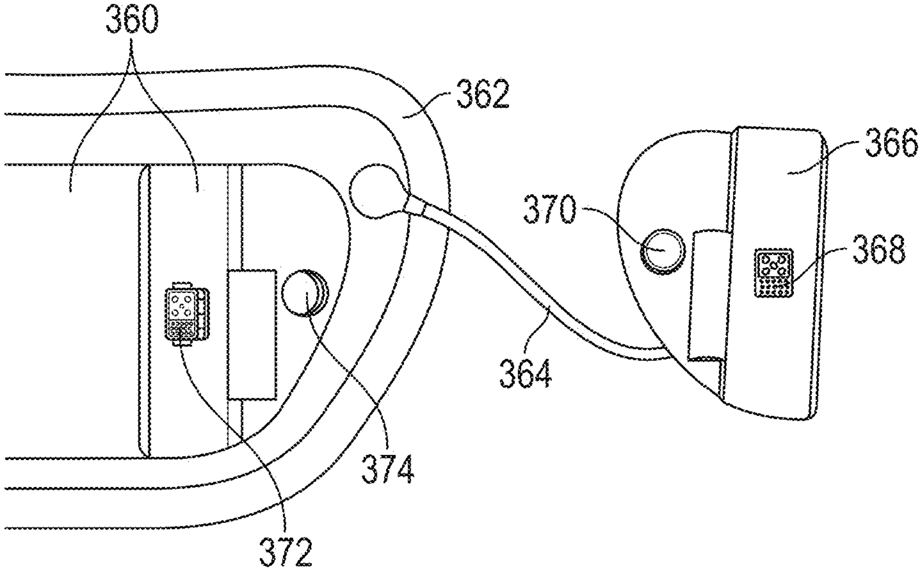
FIG. 21 shows a partial view of an embodiment of a wearable device having a reusable component mechanically attached in a detachable manner to an adhesive flexible engagement substrate of the device's disposable component.

FIG. 21 shows a partial view of an embodiment of a wearable device (such as a cardiopulmonary physiologic monitor or cardioverter/defibrillator similar to those shown in WO2017/035502) having a reusable component (e.g., housings 360 containing cardiopulmonary physiologic monitor or defibrillator components) mechanically attached in a detachable manner to an adhesive flexible engagement substrate 362 of the device's disposable component. Other parts of the disposable component include cable 364 and battery housing 366 containing one or more batteries. Battery housing 366 has an electrical connector 368 and a mechanical connector 370 which may be connected and disconnected to an electrical connector 372 and a mechanical connector 374, respectively, on the housings 360. Once connected, connectors 372 and 368 and cable 364 electrically connect the cardiopulmonary physiologic monitor or defibrillator components within housings 360 to electrodes on the bottom side of patient engagement substrate 362 and a second patient engagement substrate (not shown), allowing for sensing of cardiac activity (such as, e.g., ECG signals) or, in the case of a defibrillator, delivery of electric shocks from electrodes on the bottom sides of the patient engagement substrates. A flexible circuit (not shown) provides electrical communication among the cardiopulmonary physiologic monitor or defibrillator components within housings 360.

In the various embodiments, the electrical connectors may be, e.g., edge card connectors (i.e., USB), spring probe connectors, Zero Insertion Force (ZIF) connectors, pin-probe insertion connectors, twist and lock connectors, etc. Sealing O-rings may be used to waterproof the electrical connection.

Figure 22A:
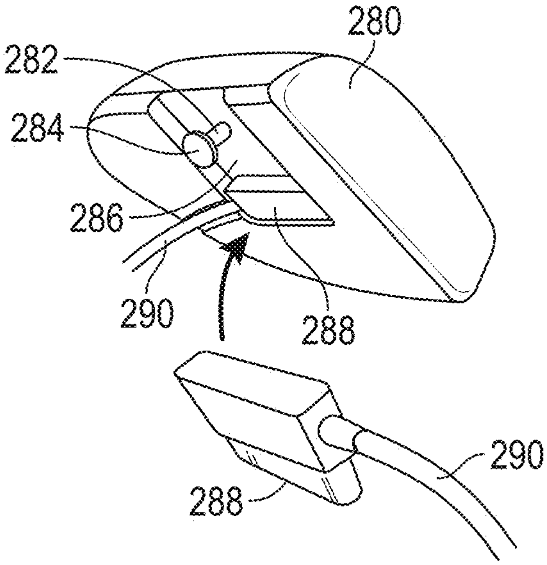
FIGS. 22A-B show another embodiment of mechanical and electrical connectors between disposable and reusable components of a wearable device.
Figure 22B:
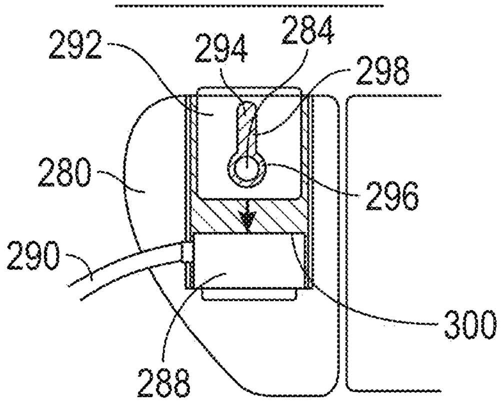

FIGS. 22A-B show another embodiment of mechanical and electrical connectors between disposable and reusable components of a wearable device, such as a cardiopulmonary physiologic monitor or cardioverter/defibrillator similar to those shown in WO2017/035502. Reusable component 280 (e.g., a housing containing cardiopulmonary physiologic monitor or defibrillator components) has a mechanical connector with a peg 282 having an enlarged end 284 disposed in a recess 286 on the bottom side of the housing. An electrical connector receptacle (not shown) is also disposed in the housing recess. As shown in FIG. 22A, an electrical connector 288 at the end of a cable 290 extending from a disposable component (e.g., an adhesive flexible engagement substrate, not shown) of the wearable device has been mated with the reusable component's electrical connector prior to mechanical connection between the reusable and disposable components. FIG. 22B is a view of the bottom side of the reusable component 280 and the mechanical connector 292 of the disposable component. Mechanical connector or lock 292 has a keyhole opening 294 with a wide portion 296 (permitting insertion of the enlarged end 284 of peg 282) and a narrow portion 298 into which peg 282 can be slid to form the mechanical connection between the components. When peg 282 is disposed in the narrow portion 298 of opening 294, a surface 300 of mechanical connector 292 engages electrical connector 288, preventing it from being disconnected from the reusable component's electrical connector.

Figure 23A:
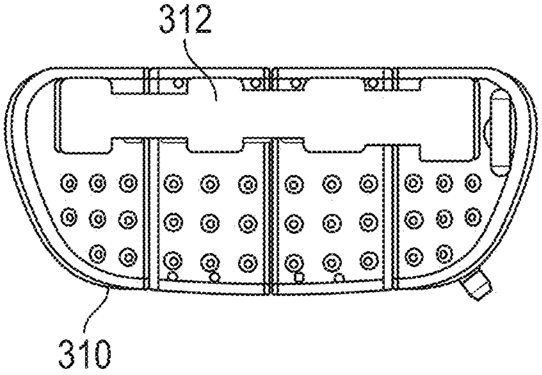
FIG. 23A-B show the bottom side of an embodiment of a reusable portion of a wearable device with four housings.
Figure 23B:
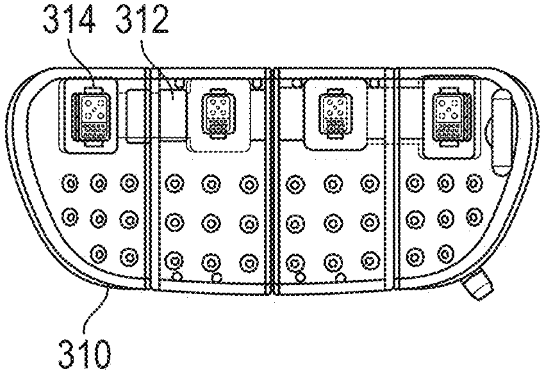

Another aspect of the invention is a flexible circuit providing a waterproof electrical communication among the electrical components (e.g., cardiopulmonary physiologic monitor or defibrillator components) in the housings of the wearable device's reusable component. The flexible circuit may also provide a robust and flexible mechanical connection between adjacent housings. FIGS. 23A-B show the bottom side of an embodiment of a reusable portion of a wearable device (such as a cardiopulmonary physiologic monitor or cardioverter/defibrillator similar to those shown in WO2017/035502) with four housings 310. Extending across the bottom surfaces of the housings 310 is a flexible circuit 312 having multiple electrical conductors (not shown) and at least one electrical connector 314 (shown in phantom in FIG. 23B) extending from the conductors in the flexible circuit to the electrical components in each of the housings 310. An overmold material (such as hot melt polyamide, polyolefin, or rubber-based thermoplastic setting adhesives) provides a robust mechanical connection between the housings while permitting flexing and other relative movement between the housings. The overmold material also has dielectric and waterproof properties enhancing the safety of the wearable device even during showering or other activities.

Figure 24:
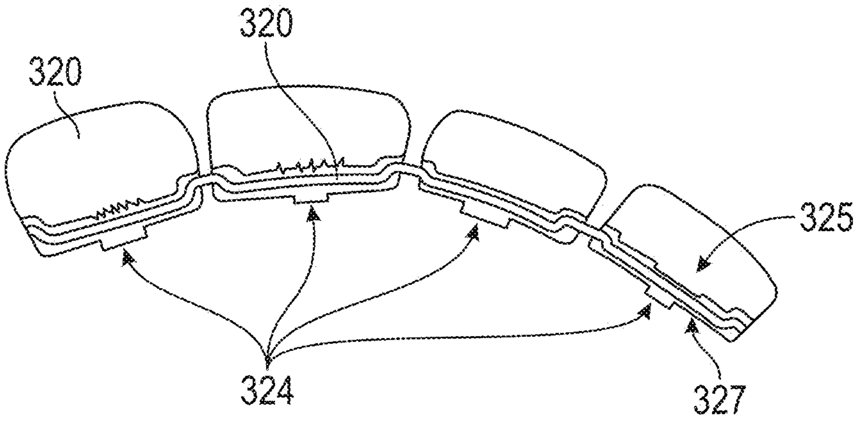
FIG. 24 shows a cut-away side view of another embodiment of a reusable component of a wearable device.

FIG. 24 shows a cut-away side view of another embodiment of a reusable component of a wearable device (such as a cardiopulmonary physiologic monitor or a cardioverter/defibrillator similar to those shown in WO2017/035502). A flexible circuit 320 extends through and between housings 322 (e.g., between housing module top 325 and housing module bottom 327). Flexible circuit 320 has multiple electrical conductors providing communication among the electrical components within the housings 322. Mechanical connectors 324 extend from the bottom sides of housings 322 to provide mechanical attachment to, and detachment from, a disposable component of the wearable device, such as an adhesive patient engagement substrate (not shown). In addition to the electrical communication, flexible circuit 320 provides a robust mechanical connection between the housings while permitting flexing and other relative movement between the housings.

Figure 36:
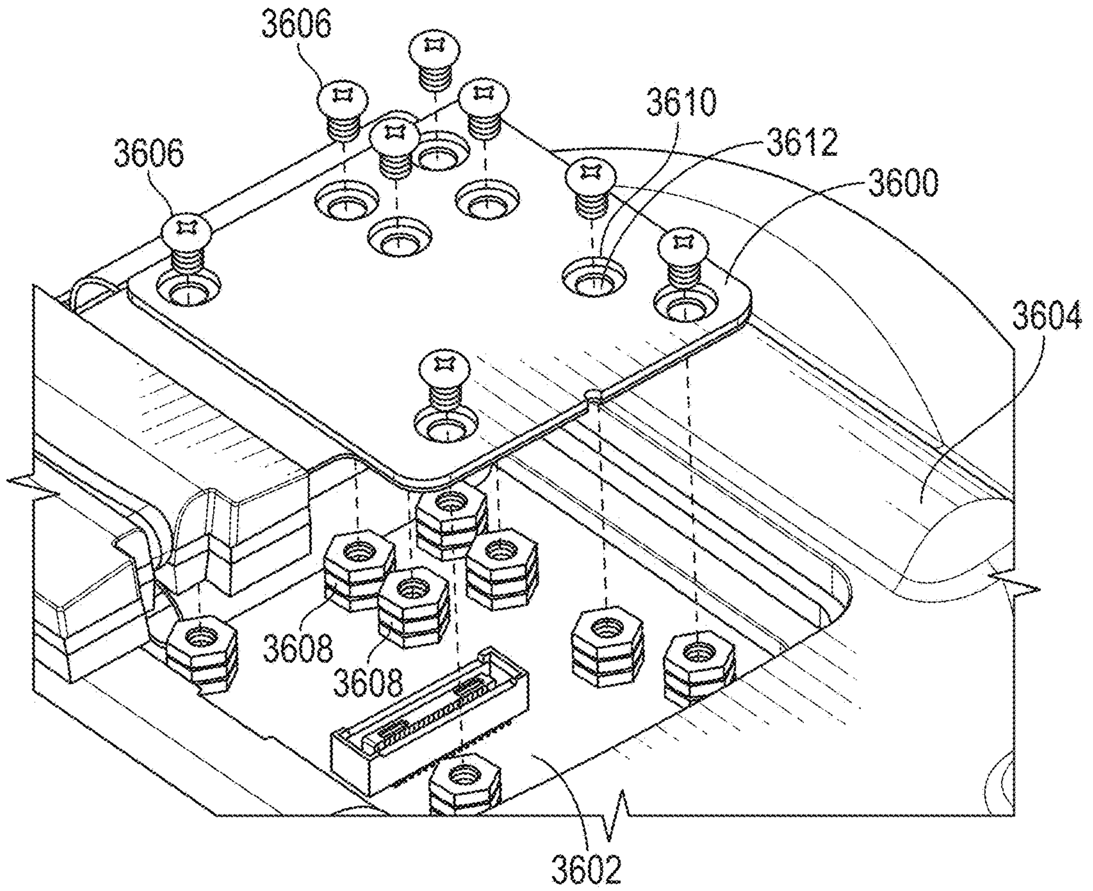
FIG. 36 shows an embodiment of an electrical connection between a flexible circuit and PCBAs in a reusable component of a wearable device.

FIG. 36 shows an embodiment of electrical connections between a flexible circuit (such as the flexible circuits described above, extending through and between housings of the wearable device's reusable component. The electrical connections between the flex circuit 3600 and the PCBAs 3602 in the housing 3604 comprise screws 3606 inserted through the flex circuit 3600 into threaded standoffs 3608 that are soldered to the PCBAs 3602. Conductive material 3610 (e.g., copper) is exposed around each through hole 3612 in the flex circuit on the top and/or bottom surfaces of the flex circuit 3600. When the screw 3606 is passed through the hole 3612 and threads into the standoff 3608, it compresses the flex circuit against the standoff, thereby making reliable electrical contact between the flex circuit 3600 and the PCBAs 3602. These connections are mechanically strong and able to conduct high-voltage and hih-current electrical signals necessary for defibrillation. Additionally, the PCBAs can also comprise a low voltage connector (e.g., a fine-pitch multi-conductor connector) that is simultaneously engaged upon compression of the flex circuit against the standoff, enabling low-voltage communication lines.

In some embodiments of the wearable device, the disposable component is a patient engagement substrate adhesively attached to a patient and the reusable component is a plurality of housings mechanically attached to the patient engagement substrate. As the patient moves, the shape of the patient engagement substrate may change. Embodiments of the invention provide mechanical connection features between the reusable and disposable components accommodating changes in shape of one of the components. FIGS.

25A-B show a wearable device (such as a cardiopulmonary physiologic monitor or a cardioverter/defibrillator similar to those shown in WO2017/035502) having a reusable component with a plurality of housings 330 connected by a flexible connection (such as a flexible circuit, as described above) and a disposable component 334 (such as an adhesive patient engagement substrate). The mechanical connectors of the reusable component include pegs 336 having enlarged ends 338. The mechanical connectors of the disposable component include slots 340, 342, 344 and 346 in positions corresponding to pegs 326. Slots 340, 344 and 346 are much wider than the width of enlarged end 338, permitting movement of enlarged end 338 within slots 340, 344 and 346 as patient engagement substrate 334 bends and straightens with the patient's movement. Anchor slot 342, on the other hand, has a width only slightly larger than enlarged end 338, so that its corresponding peg moves only slightly or not at all as the other pegs move within their slots. This arrangement permits some relative movement between the reusable and disposable components of the wearable device without causing complete mechanical disconnection of the components.

Figure 26A:
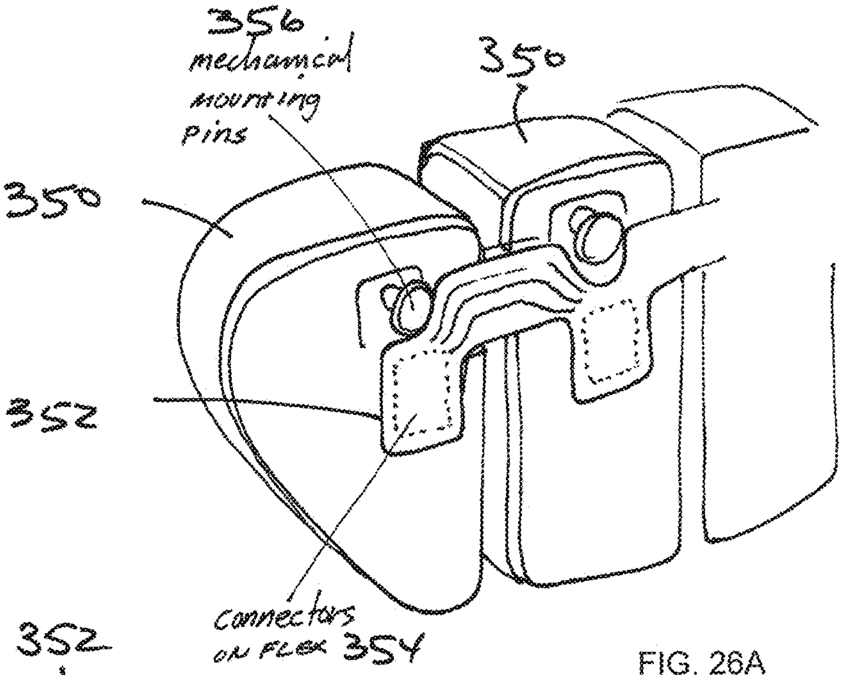
FIGS. 26A-B show partial views of the reusable component of a wearable device having a plurality of housings mechanically and electrically connected by a flexible circuit having electrical connections extending into the housings.
Figure 26B:
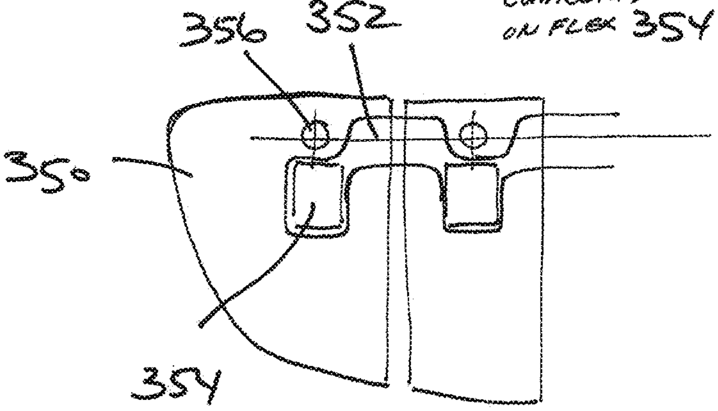

FIGS. 26A-B show partial views of the reusable component of a wearable device (such as a cardiopulmonary physiologic monitor or a cardioverter/defibrillator similar to those shown in WO2017/035502) having a plurality of housings 350 (each containing, e.g., one or more of a controller, a capacitor or a battery) mechanically and electrically connected by a flexible circuit 352 having electrical connections 354 extending into the housings 350. Mechanical connectors 356 project from the back sides of housings 350 from positions above the flexible circuit 352. This arrangement of mechanical connectors and flexible circuit reduces the overall height of the reusable component.

In embodiments of the invention, the disposable component of the wearable device includes a replaceable battery. For example, as discussed above with respect to FIGS. 1A-D, the battery housing is part of the disposable component that may be electrically and mechanically connected to, and disconnected from, the reusable component of the wearable device.

Figure 27A:
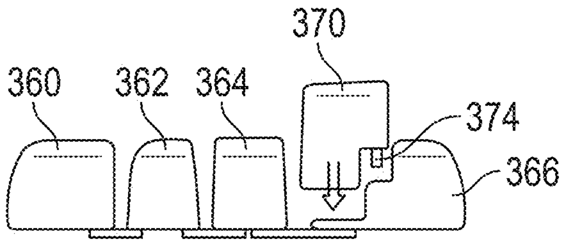
FIGS. 27A-B show an embodiment of a reusable component of a wearable device having a plurality of housings mechanically and electrically connected by a flexible circuit.
Figure 27B:
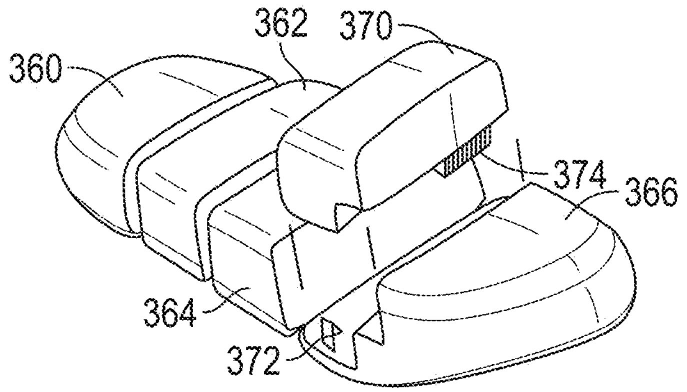

FIGS. 27A-B show an embodiment of a reusable component of a wearable device (such as a cardiopulmonary physiologic monitor or a cardioverter/defibrillator similar to those shown in WO2017/035502) having a plurality of housings 360, 362, 364 and 366 mechanically and electrically connected by a flexible circuit 368. The disposable component of the wearable device includes a battery housing 370. A reusable component mechanical connector or lock 372 extends from a surface of housing 366; battery housing 370 has a corresponding mechanical connector (not shown). Battery housing also has an electrical connector 374, and housing 366 has a corresponding electrical connector (not shown). The electrical and mechanical connections between battery housing 370 and reusable component housing 366 occur simultaneously.

Figure 28:
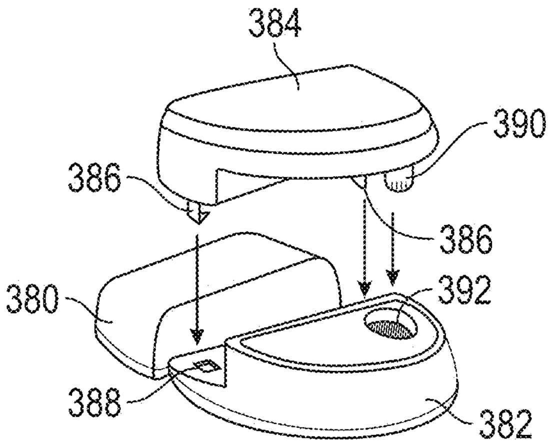
FIG. 28 shows a partial view of another embodiment of a reusable component of a wearable device having a plurality of housings mechanically and electrically connected by a flexible circuit.

FIG. 28 shows a partial view of another embodiment of a reusable component of a wearable device (such as a cardiopulmonary physiologic monitor or a cardioverter/defibrillator similar to those shown in WO2017/035502) having a plurality of housings 380 and 382 mechanically and electrically connected by a flexible circuit (not shown). The disposable component of the wearable device includes a battery housing 384. Reusable component mechanical connectors or locks 388 are disposed in housing 382 (only one is shown in FIG. 28); battery housing 384 has corresponding mechanical connectors 386 that can latch to lock 388. Battery housing also has an electrical connector 390, and housing 382 has a corresponding electrical connector 392. The electrical and mechanical connections between battery housing 384 and reusable component housing 382 occur simultaneously.

Figure 37:
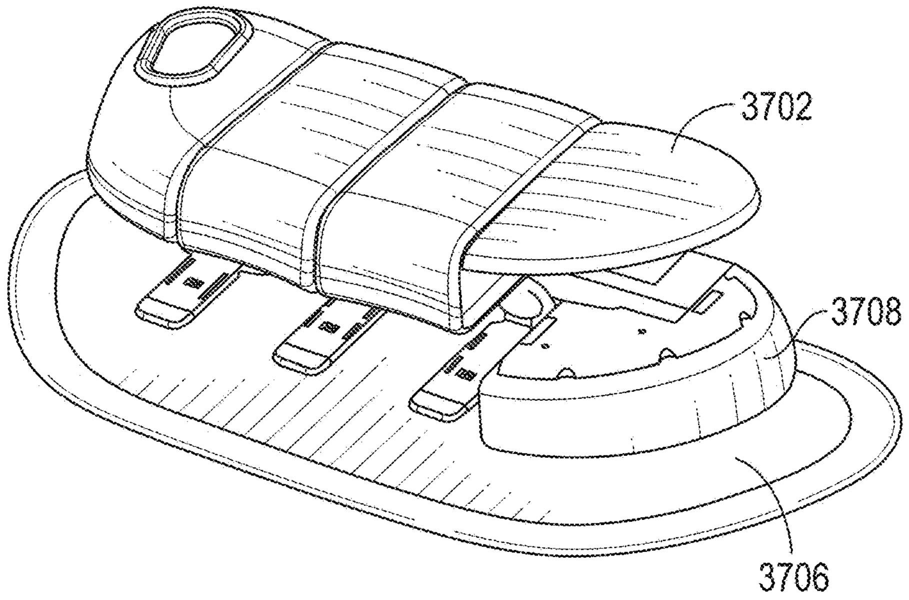
FIG. 37 shows an embodiment of interaction between a reusable component of a wearable device and a disposable component and attached battery of the wearable device.

FIG. 37 shows an embodiment of a reusable component of a wearable device (such as a cardiopulmonary physiologic monitor or a cardioverter/defibrillator similar to those shown in WO2017/035502) having a plurality of housings 3702 mechanically and electrically connected by a flexible circuit (not shown). The disposable component 3706 of the wearable device is mechanically connected to a disposable battery 3708. The connection between the disposable component and the battery can be permanent, such that the battery is disposed of along with the disposable component. The reusable component modules can be configured to be lowered onto the disposable component and battery such that they make an electrical connection, and a mechanical connection to hold onto the battery module. The reusable component can be lifted off of the battery and disposable component prior to disposal of the disposable component.

Figure 29:
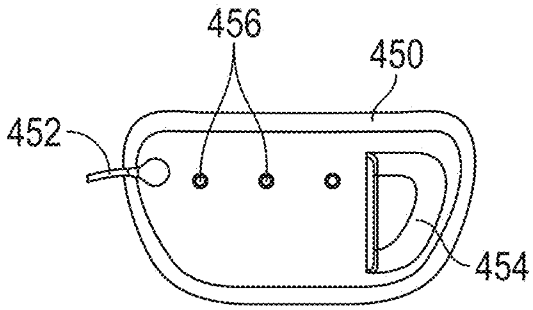
FIG. 29 shows aspects of a disposable component of a wearable device (such as a cardiopulmonary physiologic monitor or a cardioverter/defibrillator.

FIG. 29 shows aspects of a disposable component of a wearable device (such as a cardiopulmonary physiologic monitor or a cardioverter/defibrillator similar to those shown in WO2017/035502). In this embodiment, the disposable component includes an adhesive patient engagement substrate 450, a cable 452 connecting to a second patient engagement substrate (not shown), a battery housing 454 containing one or more batteries, and a plurality of mechanical connectors 456 for connecting to corresponding mechanical connectors on a reusable component of the wearable device. The battery housing also has an electrical connector (not shown) configured to mate with a corresponding electrical connector in the reusable component for providing electrical communication between the electrical components in the reusable component and the battery and other electrical components of the disposable component, such as an electrode disposed on the bottom side of the patient engagement substrate.

Figure 30A:
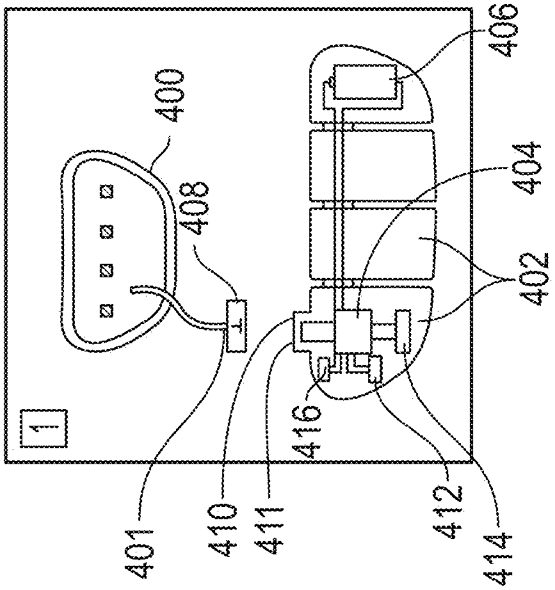
FIG. 30A-B show an embodiment of a wearable device in which the disposable component includes an adhesive patient engagement substrate and a cable, and the reusable component includes a plurality of housings each containing one or more of a controller, a battery or a capacitor.
Figure 30B:
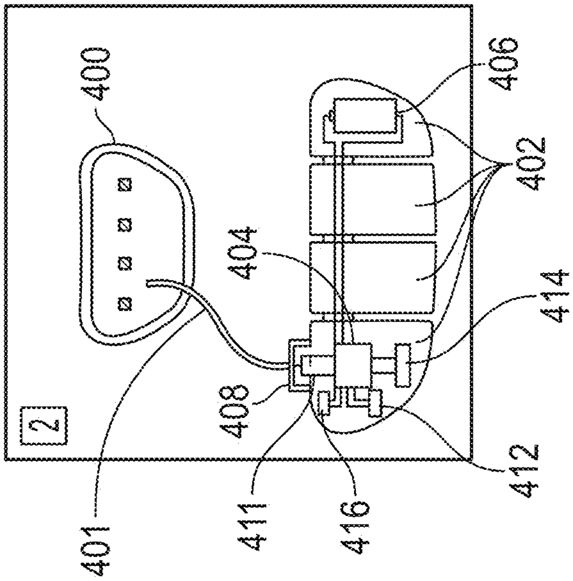

FIGS. 30A-B show an embodiment of a wearable device (such as a cardiopulmonary physiologic monitor or a cardioverter/defibrillator similar to those shown in WO2017/035502) in which the disposable component includes an adhesive patient engagement substrate 400 and a cable 401, and the reusable component (cutaway view) includes a plurality of housings 402 each containing one or more of a controller (e.g., microprocessor) 404, a battery 406 or a capacitor. An electrical connector 408 on cable 401 connects to a corresponding electrical connector 410 on one of the housings 402. In this embodiment, connection of electrical connectors 408 and 410 closes a circuit to provide an alert via a vibration motor 412, a speaker 414 and/or a light (e.g., LED) 416 to show that the electrical connection has been made. A contact sensor 411 can be used to determine status of electrical connection based on whether it is open (FIG. 30A) or closed (FIG. 30B).

Figure 31A:
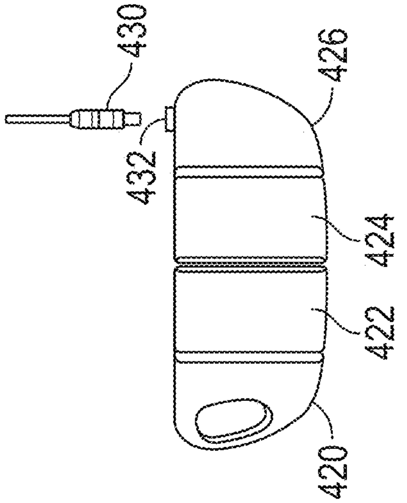
FIGS. 31A-B show an embodiment of a wearable device having a rechargeable battery in which the reusable component has a plurality of housings.
Figure 31B:
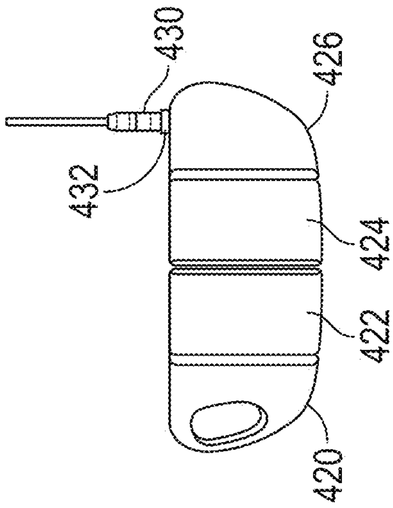
Figure 32A:
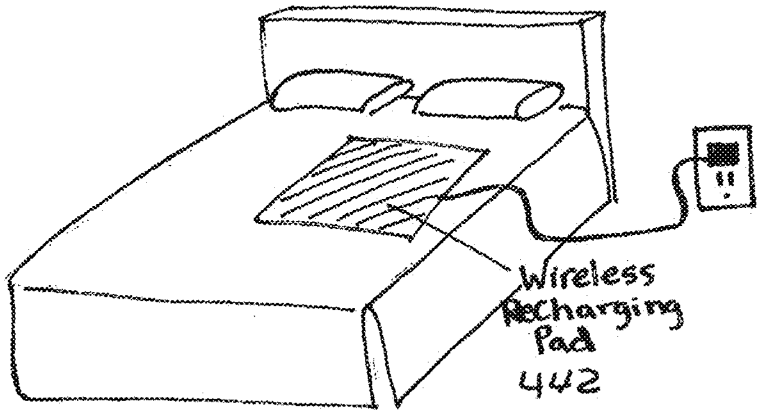
FIGS. 32A-B show an embodiment of a wearable device having a rechargeable battery in which the battery may be charged wirelessly via a charging pad while the patient is wearing the wearable device.
Figure 32B:
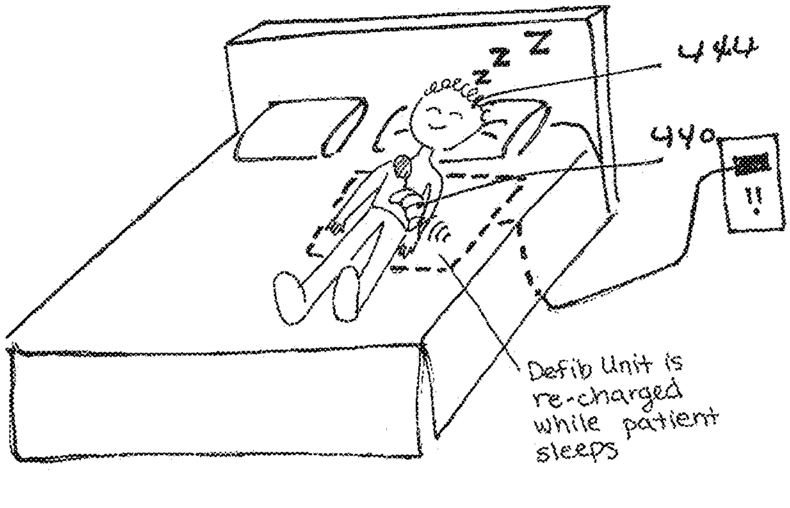

In some embodiments of the wearable device, the battery is a rechargeable battery and is part of the reusable component. For example, in the embodiment shown in FIGS. 31A-B, the reusable component has a plurality of housings 420, 422, 424 and 426. The rechargeable battery is disposed in housing 426, and it can be charged by inserting a charger connector 430 connected to a charger (not shown) into a port 432 in housing 426. In another embodiment, shown in FIGS. 32A-B, the rechargeable battery in the reusable component 440 may be charged wirelessly via a charging pad 442 while the patient 444 is wearing the wearable device.

FIGS. 34A-F show yet another embodiment of mechanical connectors for connecting and disconnecting a reusable component 600 (such as cardiopulmonary physiologic monitor or defibrillator housings 602) of a wearable device (such as an external cardioverter/defibrillator similar to those shown in WO2017/035502) to a disposable component (such as an adhesive patient engagement substrate 603) of the wearable device. In this embodiment, the disposable component mechanical connector has a latch 608 supported by a latch support 606 extending from a base 604. A spring 610 biases the latch 608 in the downward position shown in FIG. 34B. The corresponding reusable component mechanical connector 614 is shown apart from the reusable component in FIGS. 34B-D. Reusable component mechanical connector 614 has an opening leading to a cavity sized and configured to receive the latch 608 and latch support 606. When reusable component mechanical connector 614 is moved in the direction of arrow 616 in FIG. 34B, its opening will make sliding contact with the lower face of latch 608, moving latch 608 upward against the action of spring 610 until the two mechanical connectors are in their mating position, shown in FIGS. 34C-D. In this position, spring 610 moves latch 608 downward to engage an inner surface of reusable component mechanical connector 614 to hold the two components together. To disconnect the reusable component from the disposable component, a removal trigger 612 can be actuated to compress spring 610 and move latch 608 upwards into latch support 606.

Figure 25A:
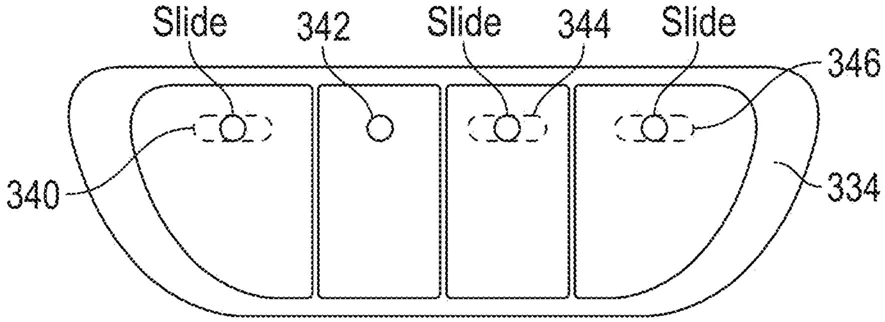
FIGS. 25A-B show a wearable device having a reusable component with a plurality of housings connected by a flexible connection.
Figure 25B:
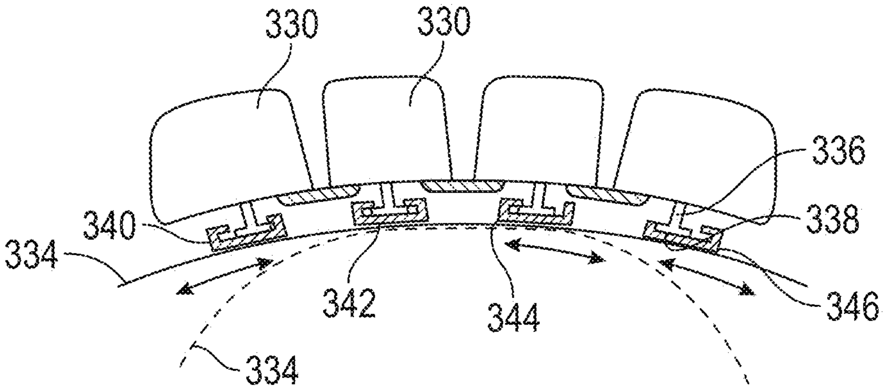
Figure 34A:
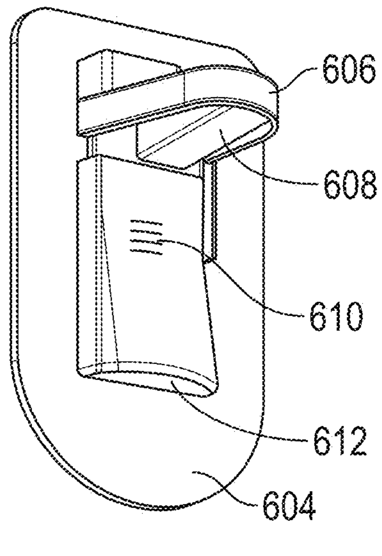
FIGS. 34A-F show yet another embodiment of mechanical connectors for connecting and disconnecting a reusable component of a wearable device to a disposable component of the wearable device.
Figure 34B:
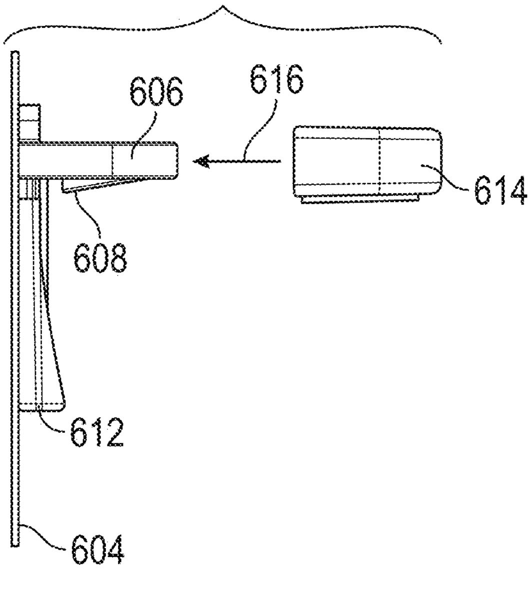
Figure 34C:
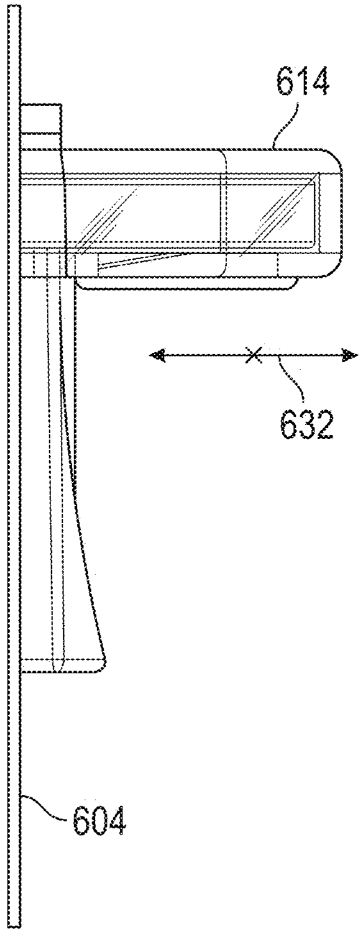
Figure 34D:
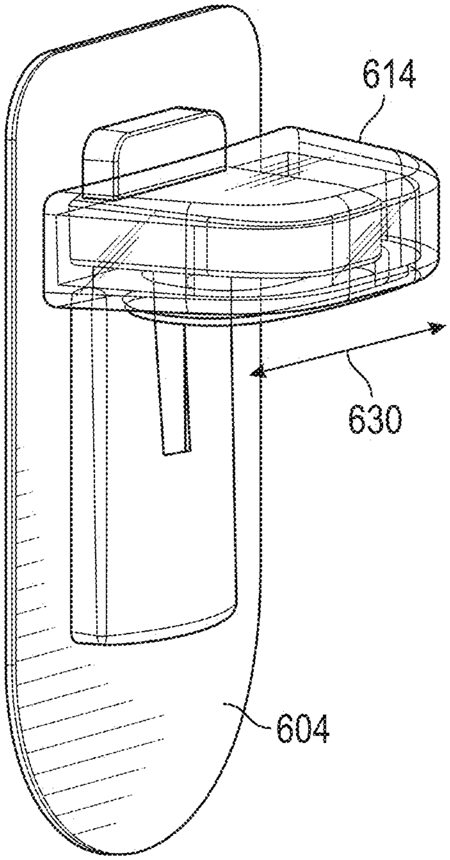

In some embodiments, the connection between the reusable component mechanical connector 614 and the disposable component connectors is that they allow motion in the direction indicated by arrows 630 shown in FIG. 34D, but constrain motion in the direction indicated by arrows 632 in FIG. 34C. This capability may be allowed by a similar concept as that described with respect to FIGS. 25A and 25B. The width of the opening in the reusable component mechanical connector can be greater than the width of the latch support, allowing sliding movement along the direction indicated by arrows 630 up to an amount equal to the difference in width between the opening in the reusable component and the widest portion of the latch support 606 positioned within the opening. This connection allows the reusable component to be held securely against the disposable component, but also allows the reusable component housings to slide back and forth during flexing caused by user movement. This capability can be very important for wear comfort and longevity of the device.

Figure 34E:
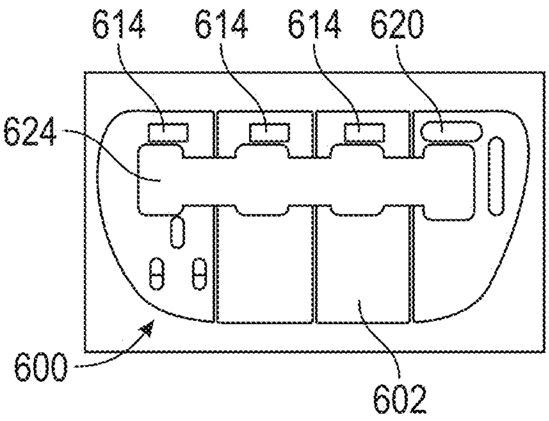
Figure 34F:
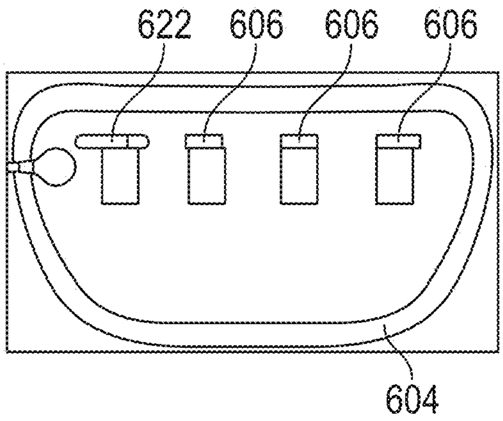

FIG. 34E shows a reusable component having four housings 602. Three of the housings have the mechanical connector 614 described with respect to FIGS. 34B-D. A fourth housing has an integrated mechanical/electrical connector 620 that mates with a corresponding mechanical/electrical connector 622 in the disposable component. A flexible circuit 624 provides electrical communication among housings 602.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable device comprising:

a reusable component and a disposable component, the disposable component comprising a patient engagement substrate comprising:

adhesive on a bottom side, an electrode on the bottom side, a disposable component electrical connector, and a disposable component mechanical connector, the reusable component comprising:

a plurality of sealed housings mechanically coupled to each other and movable with respect to each other, each of the plurality of housings containing one or more electrical components, a reusable component mechanical connector adapted to removably connect to the disposable component mechanical connector, and a reusable component electrical connector adapted to removably connect to the disposable component electrical connector, wherein when the reusable component is mechanically attached to the disposable component, the reusable component can pivot away relative to the disposable component, thereby providing more movement flexibility while the wearable device is worn by a patient.

2. The wearable device of claim 1, wherein the disposable component mechanical connector is disposed on a support element pivotably attached to the patient engagement substrate, thereby allowing the reusable component to pivot away relative to the reusable component.

3. The wearable device of claim 1, wherein at least one of the reusable component mechanical connector and the disposable component mechanical connector are exposed when the reusable component is pivoted away relative to the disposable component.

4. The wearable device of claim 1, wherein the reusable component can pivot away relative to the disposable component from a first position to a second position, wherein the reusable component mechanical connector can be manually removed from the disposable component mechanical connector, and the reusable component electrical connector can be manually removed from the disposable component electrical connector when the reusable component is in the second position but not when in the first position.

5. The wearable device of claim 4, wherein the reusable component can only be separated from the disposable component after the reusable component has been pivoted from the first position to the second position and the reusable component mechanical connector has been removed from the disposable component mechanical connector.

6. The wearable device of claim 1, wherein the disposable component further comprises a battery disposed in a battery housing, a battery electrical connector configured to be connected to, and disconnected from, the reusable component electrical connector, and a battery mechanical connector adapted to removably connect the battery housing to the reusable component.

7. The wearable device of claim 1, wherein the reusable component further comprises a rechargeable battery.

8. The wearable device of claim 1, wherein the reusable component further comprises a housing support, the housings being mechanically connected to a top side of the housing support, the reusable component mechanical connector being disposed on a bottom side of the housing support.

9. The wearable device of claim 1, wherein the disposable component mechanical connector comprises a spring-biased latch and the reusable component mechanical connector comprises a cavity adapted to receive the latch.

10. The wearable device of claim 1, wherein the disposable component mechanical connector and the reusable component mechanical connector are configured to allow the reusable component and the disposable component to move laterally relative to one another while still maintaining a mechanical connection.

11. The wearable device of claim 1, wherein the patient engagement substrate has a first configuration in which a connection between the disposable component mechanical connector and the reusable component mechanical connector is maintained and a second configuration in which the disposable component mechanical connector may be disconnected from the reusable component mechanical connector.

12. The wearable device of claim 1, wherein the disposable component mechanical connector and the reusable component mechanical connector together comprise a removable component adapted to disconnect the disposable component mechanical connector from the reusable component mechanical connector.

13. The wearable device of claim 1, wherein, when connected, the disposable component electrical connector and the reusable component electrical connector provide a waterproof electrical connection.

14. The wearable device of claim 1, wherein the disposable component electrical connector is integrated with the disposable component mechanical connector and the reusable component electrical connector is integrated with the reusable component mechanical connector.

15. The wearable device of claim 1, further comprising a mechanical connection indicator adapted to indicate a mechanical connection between the disposable component mechanical connector and the reusable component mechanical connector.

16. The wearable device of claim 1, further comprising an electrical connection indicator adapted to indicate an electrical connection between the disposable component electrical connector and the reusable component electrical connector.

17. The wearable device of claim 1, wherein the disposable component further comprises a second patient engagement substrate having an electrode on a bottom side.

18. The wearable device of claim 1, wherein the wearable device comprises a cardiopulmonary physiologic monitor.

19. The wearable device of claim 1, wherein the wearable device comprises an automatic external defibrillator.

20. The wearable device of claim 1, wherein the reusable component mechanical connector and the disposable component mechanical connector comprise a trigger prevention mechanism configured to prevent disconnection of the reusable component mechanical connector and the disposable component mechanical connector.

21. The wearable device of claim 1, wherein, when connected, the disposable component electrical connector and the reusable component electrical connector provide a water-resistant electrical connection.

* * * * *